(12) United States Patent
Beauchamps et al.

(10) Patent No.: US 11,312,699 B2
(45) Date of Patent: Apr. 26, 2022

(54) PROCESSES FOR PREPARING 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE

(71) Applicant: Celgene Corporation, Summit, NJ (US)

(72) Inventors: Marie G. Beauchamps, Randolph, NJ (US); Gregg Feigelson, Chester, NY (US); Jianxin Han, Green Brook, NJ (US); Joshua Hansen, La Jolla, CA (US); Mohit A. Kothare, Bridgewater, NJ (US); Michael James Williams, Morris Plains, NJ (US); Michael J. Zacuto, Jersey City, NJ (US); Weihong Zhang, Highland Park, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 17/112,802

(22) Filed: Dec. 4, 2020

(65) Prior Publication Data

US 2021/0171493 A1 Jun. 10, 2021

Related U.S. Application Data

(60) Provisional application No. 62/945,013, filed on Dec. 6, 2019.

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC .................................................... C07D 401/04
See application file for complete search history.

(56) References Cited

U.S. PATENT DOCUMENTS

| | | |
|---|---|---|
| 5,468,881 A | 11/1995 | Ebata et al. |
| 6,248,925 B1 | 6/2001 | Ford et al. |
| 6,753,433 B2 | 6/2004 | Hilden et al. |
| 8,907,132 B2 | 12/2014 | Reddy et al. |
| 9,499,514 B2 | 11/2016 | Hansen et al. |
| 9,808,451 B2 | 11/2017 | Cathers et al. |
| 9,968,596 B2 | 5/2018 | Cathers et al. |
| 10,052,315 B2 | 8/2018 | Hui et al. |
| 10,189,808 B2 | 1/2019 | Fernandez et al. |
| 10,245,258 B2 | 4/2019 | Carrancio et al. |
| 10,449,187 B2 | 10/2019 | Hui et al. |
| 10,626,101 B2 | 4/2020 | Li et al. |
| 11,129,821 B2 | 9/2021 | Hui et al. |
| 2008/0200648 A1 | 8/2008 | Giraud et al. |
| 2018/0221361 A1 | 8/2018 | Cathers et al. |
| 2019/0003018 A1 | 1/2019 | Wakaguri et al. |
| 2019/0106405 A1 | 4/2019 | Fernandez et al. |
| 2019/0175573 A1 | 6/2019 | Carrancio et al. |
| 2020/0163948 A1 | 5/2020 | Cathers et al. |
| 2020/0206212 A1 | 7/2020 | Fernandez et al. |
| 2021/0040064 A1 | 2/2021 | Fernandez et al. |
| 2021/0069356 A1 | 3/2021 | Hansen et al. |
| 2021/0128545 A1 | 5/2021 | Buccholz et al. |
| 2021/0154182 A1 | 5/2021 | Carrancio et al. |

FOREIGN PATENT DOCUMENTS

| | | |
|---|---|---|
| WO | WO 1997/019074 A | 5/1997 |
| WO | WO 2021/188387 | 9/2021 |

OTHER PUBLICATIONS

Bernstein et al., "16-Hydroxylated Steroids. XXIII. 1 21-Chloro-16α-hydroxycorticoids and Their 16α, 17α-Acetonides." The Journal of Organic Chemistry 27.2 (1962): 690-692.

Leggio et al., "One-pot synthesis of amides from carboxylic acids activated using thionyl chloride." Rsc Advances 6.41 (2016): 34468-34475.

*Primary Examiner* — Patricia L Morris
(74) *Attorney, Agent, or Firm* — Jones Day

(57) ABSTRACT

Provided herein are processes for preparing 2-(4-chlorophenyl)-N-((2-(2,6-dioxopiperidin-3-yl)-1-oxoisoindolin-5-yl)methyl)-2,2-difluoroacetamide.

24 Claims, 7 Drawing Sheets

PROCESSES FOR PREPARING 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE

RELATED APPLICATIONS

This application claims the benefit of U.S. Provisional Application No. 62/945,013, filed Dec. 6, 2019, the disclosure of which is incorporated herein by reference in its entirety.

FIELD

Provided herein are processes for preparing 2-(4-chlorophenyl)-N-((2-(2,6-dioxopiperidin-3-yl)-1-oxoisoindolin-5-yl)methyl)-2,2-difluoroacetamide.

BACKGROUND 2-(4-Chlorophenyl)-N-((2-(2,6-dioxopiperidin-3-yl)-1-oxoisoindolin-5-yl)methyl)-2,2-difluoroacetamide or a stereoisomer or mixture of stereoisomers, pharmaceutically acceptable salt, tautomer, prodrug, solvate, hydrate, cocrystal, clathrate, or polymorph thereof has been shown to have anti-cancer activities. Exemplary formulations of the compound, methods of use and methods of synthesis of the compound are disclosed in U.S. Pat. Nos. 9,499,514 B2; 9,968,596 B2; 9,808,451 B2; 10,052,315 B2; 10,189,808 B2; and 10,245,258 B2; and U.S. Patent Publication Nos. US-2018-0221361-A1; US-2018-0353496-A1; US-2019-0106405-A1 and US-2019-0175573-A1; and U.S. application Ser. No. 16/436,819, filed on Jun. 10, 2019; Ser. No. 16/024,581, filed on Jun. 29, 2018; and 62/787,034, filed on Dec. 31, 2018, the disclosure of each of which is incorporated herein by reference in its entirety.

There is a need for a more efficient, commercially viable, safe, less toxic, and environmentally friendly process for synthesis of 2-(4-chlorophenyl)-N-((2-(2,6-dioxopiperidin-3-yl)-1-oxoisoindolin-5-yl)methyl)-2,2-difluoroacetamide (Compound 1).

BRIEF SUMMARY

Provided herein are efficient processes for preparing Compound 1. In one embodiment, provided herein is a process for preparing a polymorph form of Compound 1. In one embodiment, provided herein is a process for preparing polymorph Form C of Compound 1.

In one embodiment, provided herein is a process for preparing Compound 1 comprising contacting an acid salt of 3-(5-(aminomethyl)-1-oxoisoindolin-2-yl)piperidine-2,6-dione with 2-(4-chlorophenyl)-2,2-difluoroacetic acid (Compound L1) with 2-(4-chlorophenyl)-2,2-difluoroacetic acid in the presence of thionyl chloride (SOCl$_2$), in a solvent under conditions suitable to provide Compound 1.

In one embodiment, provided herein is a process for preparing Compound 1, comprising a step of contacting Compound L

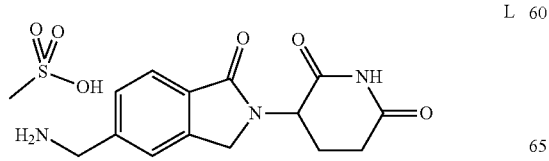

with 2-(4-chlorophenyl)-2,2-difluoroacetic acid under conditions suitable to provide Compound 1.

In one embodiment, provided herein is a process for preparing Compound L, comprising contacting Compound G

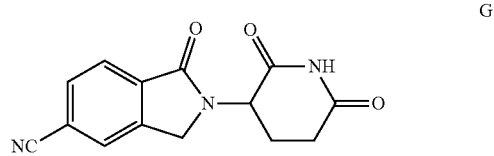 [SMILES: N#Cc1ccc2c(c1)CN(C1CCC(=O)NC1=O)C2=O]

with a reducing agent and methanesulfonic acid under conditions suitable to provide Compound L

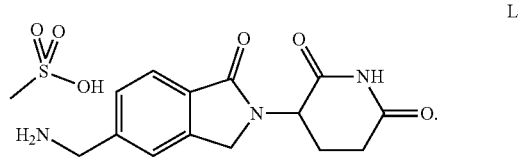

In one embodiment, provided herein is a process for preparing Compound G comprising contacting Compound X

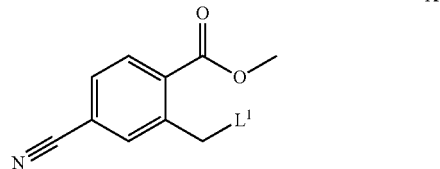

wherein L$^1$ is a leaving group, with 3-aminopiperidine-2,6-dione hydrochloride, under conditions suitable to provide Compound G

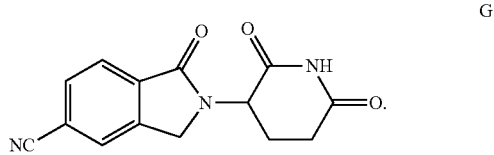 [SMILES: N#Cc1ccc2c(c1)CN(C1CCC(=O)NC1=O)C2=O]

In one embodiment, provided herein is a process for preparing Compound G, comprising contacting Compound D

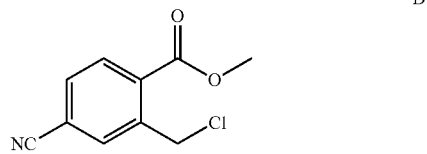

with 3-aminopiperidine-2,6-dione hydrochloride under conditions suitable to provide Compound G

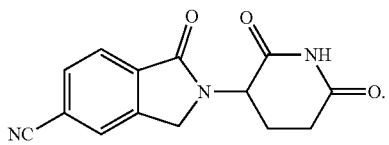

In one embodiment, provided herein is a process for preparing Compound 1 comprising
a) contacting Compound X

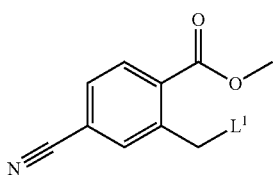

wherein L¹ is a leaving group, with 3-aminopiperidine-2,6-dione hydrochloride under conditions suitable to provide Compound G,

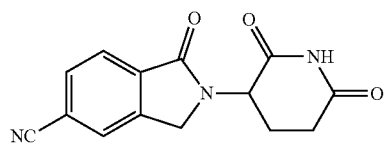

b) contacting Compound G with a reducing agent and methanesulfonic acid under conditions suitable to provide Compound L

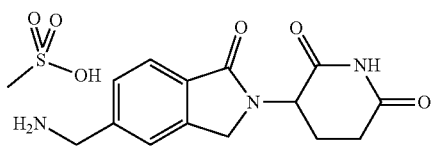

and c) contacting Compound L with 2-(4-chlorophenyl)-2,2-difluoroacetic acid under conditions suitable to provide Compound 1. In one embodiment, L¹ is a halogen or methanesulfonate. In one embodiment, L¹ is chloro or methanesulfonate.

In one embodiment, provided herein is a process for preparing Compound 1 comprising
a) contacting Compound D

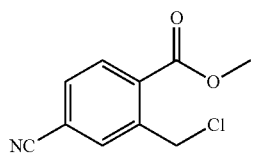

with 3-aminopiperidine-2,6-dione hydrochloride under conditions suitable to provide Compound G,

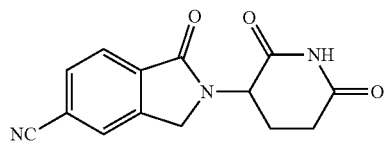

b) contacting Compound G with a reducing agent and methanesulfonic acid under conditions suitable to provide Compound L

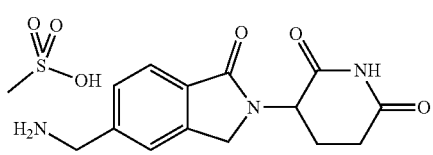

and c) contacting Compound L with 2-(4-chlorophenyl)-2,2-difluoroacetic acid under conditions suitable to provide Compound 1.

Further provided herein are chemical intermediates useful in the processes provided herein.

Compound 1 is useful in methods of treating cancer. Also disclosed is Compound 1 for use in methods of treating cancer. In one embodiment, the cancer is a solid tumor or a hematological cancer.

These and other aspects of the subject matter described herein will become evident upon reference to the following detailed description.

DETAILED DESCRIPTION

Definitions

Figure 1:
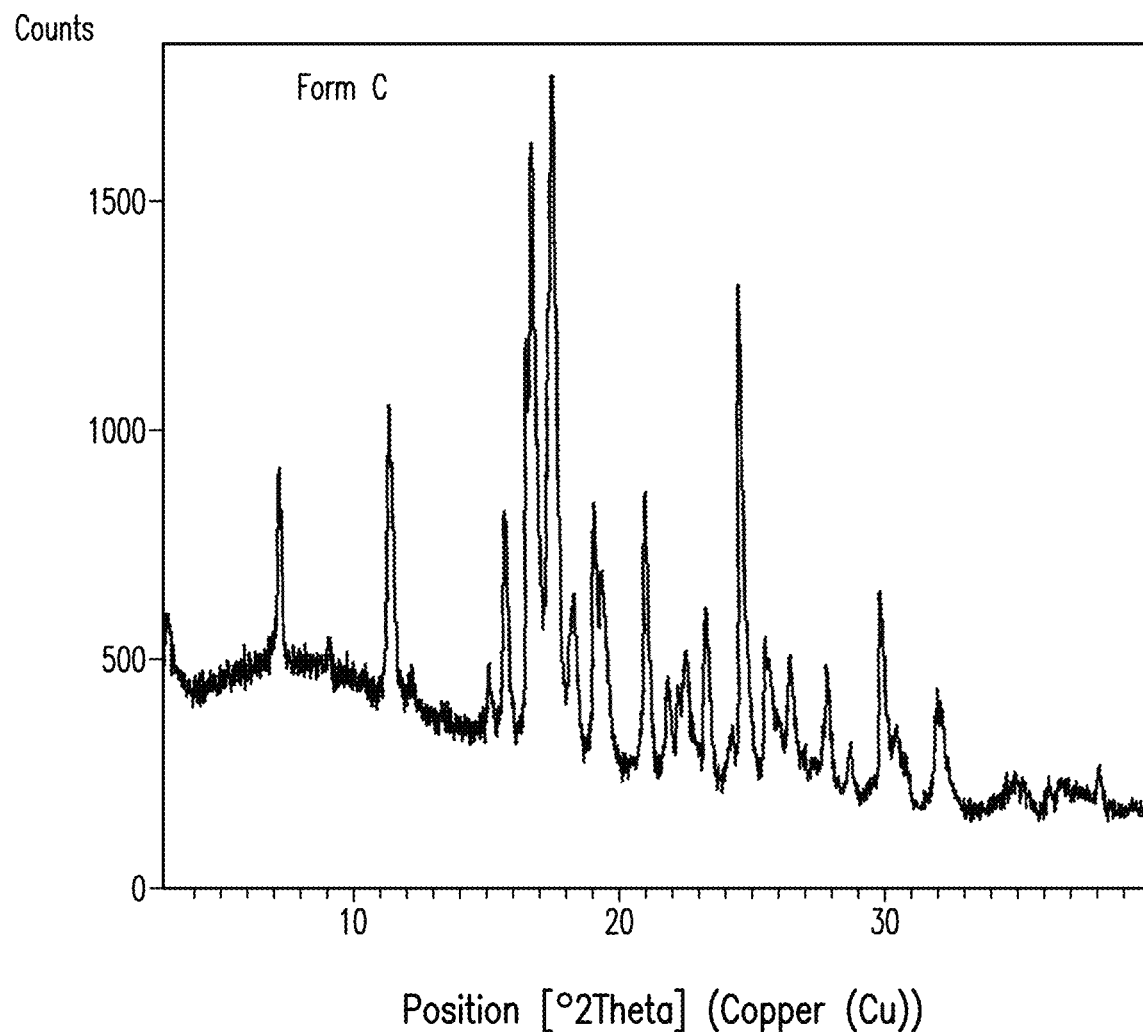
FIG. 1 depicts an XRPD plot of polymorph Form C of 2-(4-chlorophenyl)-N-((2-(2,6-dioxopiperidin-3-yl)-1-oxoisoindolin-5-yl)methyl)-2,2-difluoroacetamide.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In general, the technical teaching of one embodiment can be combined with that disclosed in other embodiments provided herein.

The use of the word "a" or "an" when used in conjunction with the term "comprising" in the claims and/or the specification can mean "one", but it is also consistent with the meaning of "one or more", "at least one" and "one or more than one."

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive. E.g., "treating, preventing or managing" or similar listings means: "treating; preventing; managing; treating and preventing; treating and managing; preventing and managing; treating, preventing and managing".

The term "Compound 1" refers to "2-(4-chlorophenyl)-N-((2-(2,6-dioxopiperidin-3-yl)-1-oxoisoindolin-5-yl)methyl)-2,2-difluoroacetamide" having the structure:

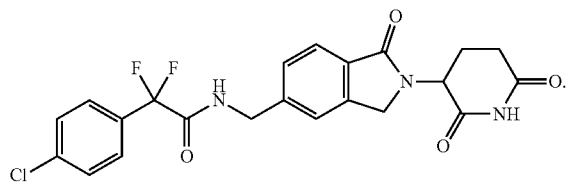 [SMILES: O=C1CCC(N2Cc3cc(CNC(=O)C(F)(F)c4ccc(Cl)cc4)ccc3C2=O)C(=O)N1]

Unless specifically stated otherwise, where a compound may assume alternative tautomeric, regioisomeric and/or stereoisomeric forms, all alternative isomers are intended to be encompassed within the scope of the claimed subject matter. For example, where a compound can have one of two tautomeric forms, it is intended that both tautomers be encompassed herein.

Thus, the compounds herein may be enantiomerically pure, or be stereoisomeric or diastereomeric mixtures. As used herein and unless otherwise indicated, the term "stereoisomerically pure" means a composition that comprises one stereoisomer of a compound and is substantially free of other stereoisomers of that compound. For example, a stereoisomerically pure composition of a compound having one chiral center will be substantially free of the opposite enantiomer of the compound. A stereoisomerically pure composition of a compound having two chiral centers will be substantially free of other diastereomers of the compound. A typical stereoisomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. A stereoisomerically pure compound as used herein comprises greater than about 80% by weight of one stereoisomer of the compound, more preferably greater than about 90% by weight of one stereoisomer of the compound, even more preferably greater than about 95% by weight of one stereoisomer of the compound, and most preferably greater than about 97% by weight of one stereoisomer of the compound. As used herein and unless otherwise indicated, the term "stereoisomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereoisomerically pure composition of a compound having one chiral center. Similarly, the term "stereoisomerically enriched" means a stereoisomerically enriched composition of a compound having one chiral center. As used herein, stereoisomeric or diastereomeric mixtures means a composition that comprises more than one stereoisomer of a compound. A typical stereoisomeric mixture of a compound comprises about 50% by weight of one stereoisomer of the compound and about 50% by weight of other stereoisomers of the compound, or comprises greater than about 50% by weight of one stereoisomer of the compound and less than about 50% by weight of other stereoisomers of the compound, or comprises greater than about 45% by weight of one stereoisomer of the compound and less than about 55% by weight of the other stereoisomers of the compound, or comprises greater than about 40% by weight of one stereoisomer of the compound and less than about 60% by weight of the other stereoisomers of the compound, or comprises greater than about 35% by weight of one stereoisomer of the compound and less than about 65% by weight of the other stereoisomers of the compound.

As used herein, the term "solid form" refers a crystal form or an amorphous form or a mixture thereof of 2-(4-chlorophenyl)-N-((2-(2,6-dioxopiperidin-3-yl)-1-oxoisoindolin-5-yl)methyl)-2,2-difluoroacetamide. In one embodiment, solid form refers to polymorph Form C of 2-(4-chlorophenyl)-N-((2-(2,6-dioxopiperidin-3-yl)-1-oxoisoindolin-5-yl)methyl)-2,2-difluoroacetamide.

It should also be noted the compounds herein can contain unnatural proportions of atomic isotopes at one or more of the atoms. For example, the compounds may be radiolabeled with radioactive isotopes, such as for example deuterium ($^2$H), tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the Compound 1 as described herein, whether radioactive or not, are intended to be encompassed within the scope of the embodiments provided herein. In some embodiments, there are provided isotopologues of Compound 1, for example, the isotopologues are deuterium, carbon-13, and/or nitrogen-15 enriched Compound 1. As used herein, "deuterated", means a compound wherein at least one hydrogen (H) has been replaced by deuterium (indicated by D or $^2$H), that is, the compound is enriched in deuterium in at least one position.

It is understood that, independently of stereoisomerical or isotopic composition, each compound referred to herein can be provided in the form of any of the pharmaceutically acceptable salts discussed herein. Equally, it is understood that the isotopic composition may vary independently from the stereoisomerical composition of each compound referred to herein. Further, the isotopic composition, while being restricted to those elements present in the respective compound or salt thereof, may otherwise vary independently from the selection of the pharmaceutically acceptable salt of the respective compound.

As used herein and unless otherwise indicated, the term "process(es) provided herein" refers to the methods disclosed herein which are useful for preparing Compound 1 provided herein. Modifications to the methods disclosed herein (e.g., starting materials, reagents, protecting groups, solvents, temperatures, reaction times, purification) are also encompassed by the present embodiments.

As used herein and unless otherwise indicated, the term "adding" or the like means contacting one reactant, reagent, solvent, catalyst, or the like with another reactant, reagent, solvent, catalyst, or the like. Reactants, reagents, solvents, catalysts, or the like can be added individually, simultaneously, or separately and can be added in any order. They can be added in the presence or absence of heat and can optionally be added under an inert atmosphere.

As used herein and unless otherwise indicated, a reaction that is "substantially complete" or is driven to "substantial completion" means that the reaction contains more than about 80% by percent yield, in one embodiment, more than about 90% by percent yield, in another embodiment, more than about 95% by percent yield, and in yet another embodiment, more than about 97% by percent yield of the desired product.

As used herein, and unless otherwise specified, the term "leaving group" refers to a stable moiety that can be detached from a molecule in a bond-breaking step. In one embodiment, the leaving group includes, but is not limited to, a halogen, such as fluoro, chloro, bromo, iodo and methanesulfonate (alternatively termed mesylate).

A "pharmaceutically acceptable excipient," refers to a substance that aids the administration of an active agent to a subject by, for example, modifying the stability of an active agent or modifying the absorption by a subject upon administration. A pharmaceutically acceptable excipient typically has no significant adverse toxicological effect on the patient. Examples of pharmaceutically acceptable excipients include, for example, water, NaCl (including salt solutions), normal saline solutions, ½ normal saline, sucrose, glucose, bulking agents, buffers, binders, fillers, disintegrants, lubricants, coatings, sweeteners, flavors, alcohols, oils, gelatins, carbohydrates such as amylose or starch, fatty acid esters, hydroxymethycellulose, polyvinyl pyrrolidine, and colors, and the like. One of skill in the art will recognize that other pharmaceutical excipients known in the art are useful in the present invention and include those listed in for example the *Handbook of Pharmaceutical Excipients*, Rowe R. C., Shesky P. J., and Quinn M. E., 6$^{th}$ Ed., The Pharmaceutical Press, RPS Publishing (2009). The terms "bulking agent", and "buffer" are used in accordance with the plain and ordinary meaning within the art.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 30%, 25%, 20%, 15%, 10%, or 5% of the specified dose, amount, or weight percent is encompassed.

As used herein, "administer" or "administration" refers to the act of physically delivering a substance as it exists outside the body into a subject. Administration includes all forms known in the art for delivering therapeutic agents, including but not limited to topical, mucosal, injections, intradermal, intravenous, intramuscular delivery or other method of physical delivery described herein or known in the art (e.g., implantation of a slow-release device, such as a mini-osmotic pump to a subject; liposomal formulations; buccal; sublingual; palatal; gingival; nasal; vaginal; rectal; intra-arteriole; intraperitoneal; intraventricular; intracranial; or transdermal).

"Anti-cancer agents" refer to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxorubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent®, sunitinib malate, and Bevacizumab) or any other cytotoxic agents (estramustine phosphate, prednimustine), hormones or hormone agonists, antagonists, partial agonists or partial antagonists, kinase inhibitors, checkpoint inhibitors, and radiation treatment.

An "effective amount" is an amount sufficient to achieve the effect for which it is administered (e.g., treat a disease or reduce one or more symptoms of a disease or condition). Thus, administration of an "amount" of a compound described herein to a subject refers to administration of "an amount effective," to achieve the desired therapeutic result. A "therapeutically effective amount" of a compound described herein for purposes herein is thus determined by such considerations as are known in the art. The term "therapeutically effective amount" of a composition described herein refers to the amount of the composition that, when administered, is sufficient to treat one or more of the symptoms of a disease described herein (e.g., cancer, for example AML, MDS, MPN or solid tumors). Administration of a compound described herein can be determined according to factors such as, for example, the disease state, age, sex, and weight of the individual. A therapeutically effective amount also refers to any toxic or detrimental effects of Compound 1 are outweighed by the therapeutically beneficial effects.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease, or lengthening the time during which the remains in remission.

As used herein, the term "tumor," refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, "hematologic malignancy" refers to cancer of the body's blood-forming and immune system-the bone marrow and lymphatic tissue. Such cancers include leukemias, lymphomas (Non-Hodgkin's Lymphoma), Hodgkin's disease (also called Hodgkin's Lymphoma) and myeloma. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders or myeloproliferative neoplasm (MPN), chronic myelogenous leukemia (CML), myelodysplastic syndrome (MDS), human lymphotropic virus-type 1 (HTLV 1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma. In one embodiment, the hematological malignancy is AML. In another embodiment, the hematological malignancy is MDS.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. 1972, 11:942-944).

If there is a discrepancy between a depicted structure and a name given that structure, the depicted structure is to be accorded more weight. Furthermore, if the stereochemistry of a structure or a portion thereof is not indicated, e.g., with bold or dashed lines, the structure or portion thereof is to be interpreted as encompassing all stereoisomers of it.

Polymorph Form C of 2-(4-chlorophenyl)-N-((2-(2, 6-dioxopiperidin-3-yl)-1-oxoisoindolin-5-yl) methyl)-2,2-difluoroacetamide Polymorph Form C of 2-(4-chlorophenyl)-N-((2-(2,6-dioxopiperidin-3-yl)-1-oxoisoindolin-5-yl)methyl)-2,2-difluoroacetamide provided herein is characterized by one or more X-ray powder diffraction peaks at a two-theta angle of approximately 7.4, 11.5, 15.8, 16.7, 16.9, 17.7, 18.4, 19.2, 19.5, 21.1, 23.4, 24.7, and 29.9, degrees 2θ as depicted in FIG. 1. In one embodiment, polymorph Form C of has one, two, three or four characteristic X-ray powder diffraction peaks at a two-theta angle of approximately 16.7, 16.9, 17.7 and 24.7 degrees 2θ. In another embodiment, polymorph Form C has one, two, three, four, five, six or seven characteristic X-ray powder diffraction peaks as set forth in Table 1. In another embodiment, polymorph C of has one, two, or three characteristic X-ray powder diffraction peaks as set forth in Table 1.

TABLE 1

X-Ray Diffraction Peaks for Form C of Compound 1

| No. | Pos. [°2Th.] | d-spacing [Å] | Rel. Int. [%] |
|---|---|---|---|
| 1 | 7.36 | 12.0091 | 32.0 |
| 2 | 9.14 | 9.6750 | 8.3 |
| 3 | 11.51 | 7.6855 | 44.7 |
| 4 | 12.22 | 7.2420 | 4.9 |
| 5 | 15.17 | 5.8398 | 8.4 |
| 6 | 15.82 | 5.6011 | 31.8 |
| 7 | 16.68 | 5.3140 | 57.1 |
| 8 | 16.92 | 5.2392 | 86.8 |
| 9 | 17.72 | 5.0057 | 100.0 |

TABLE 1-continued

X-Ray Diffraction Peaks for Form C of Compound 1

| No. | Pos. [°2Th.] | d-spacing [Å] | Rel. Int. [%] |
| --- | --- | --- | --- |
| 10 | 18.39 | 4.8242 | 21.9 |
| 11 | 19.18 | 4.6268 | 36.4 |
| 12 | 19.45 | 4.5649 | 27.1 |
| 13 | 21.11 | 4.2077 | 40.4 |
| 14 | 21.82 | 4.0724 | 12.4 |
| 15 | 22.28 | 3.9902 | 12.0 |
| 16 | 22.57 | 3.9398 | 17.6 |
| 17 | 23.36 | 3.8082 | 24.7 |
| 18 | 24.26 | 3.6695 | 7.1 |
| 19 | 24.71 | 3.6026 | 72.5 |
| 20 | 25.74 | 3.4615 | 16.9 |
| 21 | 26.03 | 3.4231 | 9.7 |
| 22 | 26.51 | 3.3627 | 17.7 |
| 23 | 27.88 | 3.1998 | 18.0 |
| 24 | 28.70 | 3.1104 | 6.9 |
| 25 | 29.91 | 2.9871 | 30.5 |
| 26 | 30.43 | 2.9375 | 10.7 |
| 27 | 30.83 | 2.9006 | 5.8 |
| 28 | 32.01 | 2.7960 | 16.6 |
| 29 | 37.94 | 2.3718 | 5.5 |

Figure 2:
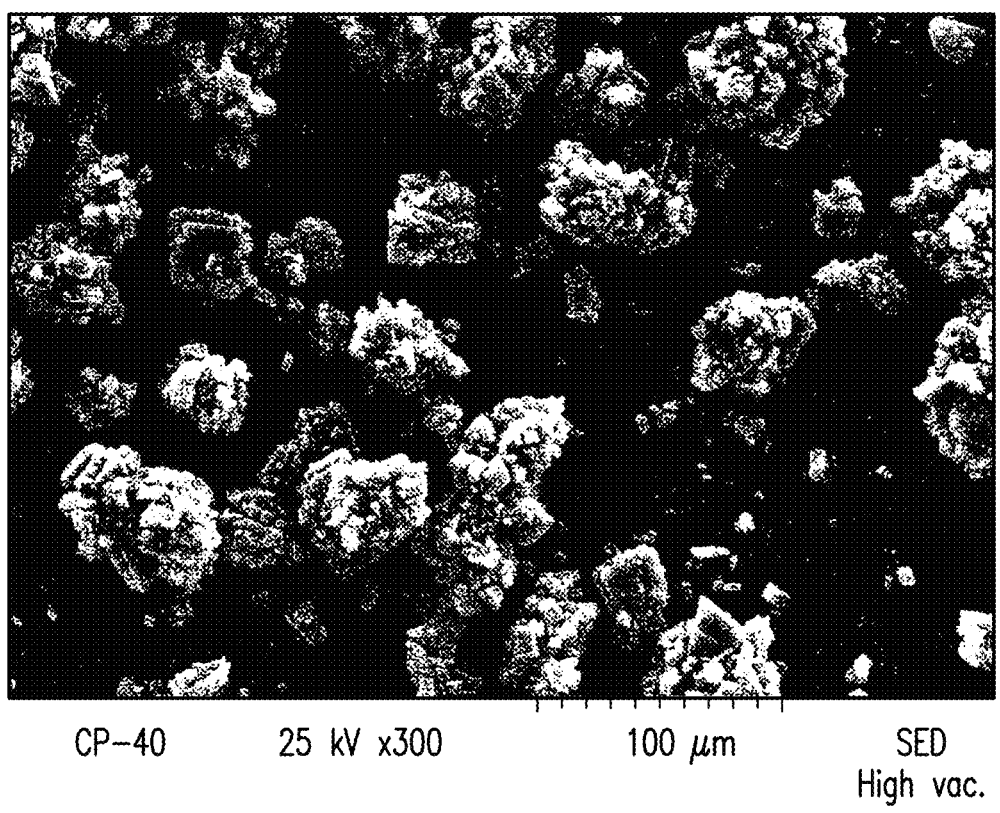
FIG. 2 depicts a SEM image of polymorph Form C of 2-(4-chlorophenyl)-N-((2-(2,6-dioxopiperidin-3-yl)-1-oxoisoindolin-5-yl)methyl)-2,2-difluoroacetamide.
Figure 3:
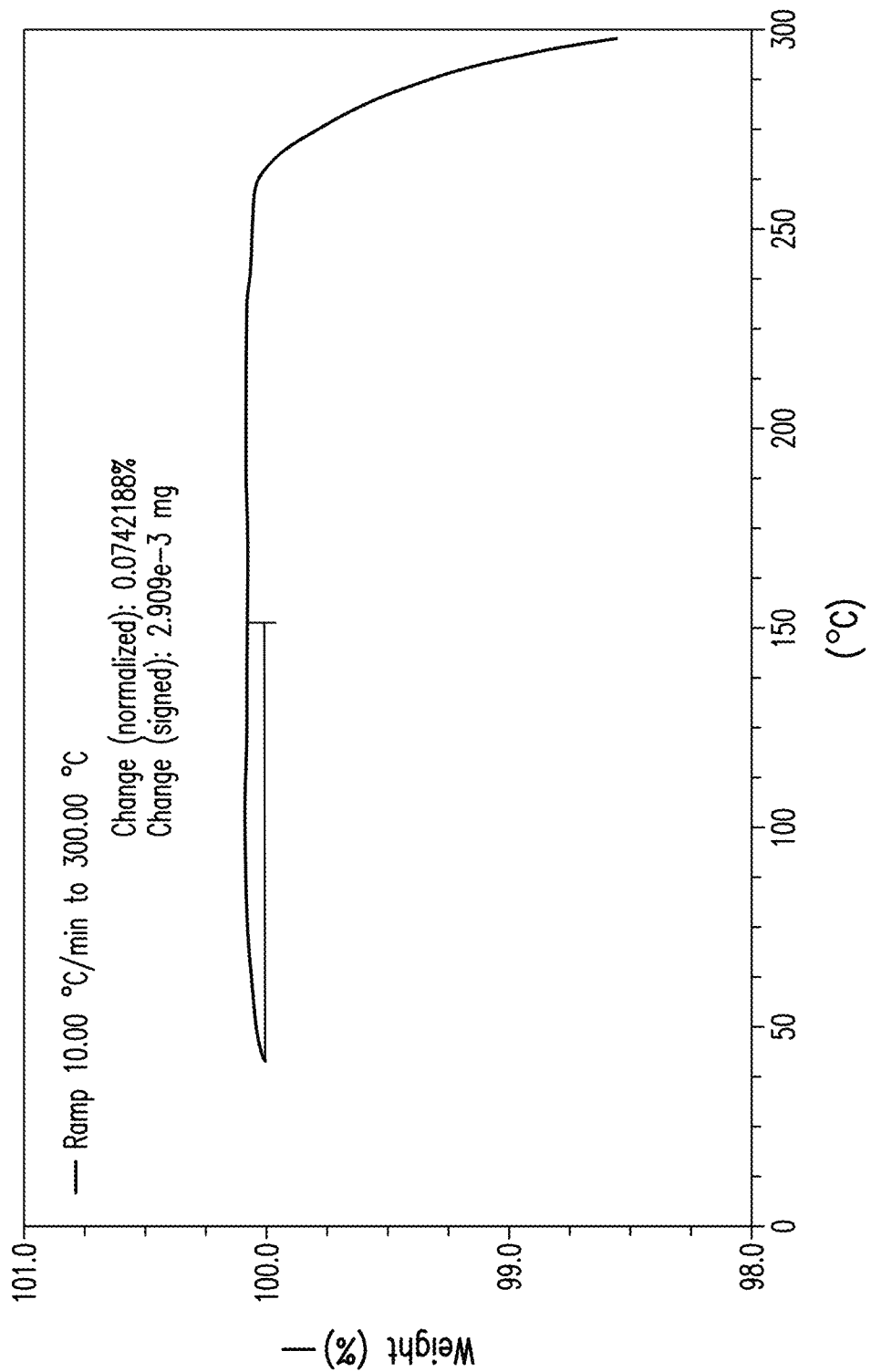
FIG. 3 depicts a TGA thermogram plot of polymorph Form C of 2-(4-chlorophenyl)-N-((2-(2,6-dioxopiperidin-3-yl)-1-oxoisoindolin-5-yl)methyl)-2,2-difluoroacetamide.

In one embodiment, polymorph Form C has the SEM picture as shown in FIG. 2. In one embodiment, polymorph Form C has a thermogravimetric (TGA) thermograph corresponding substantially to the representative TGA thermogram as depicted in FIG. 3. In certain embodiments, polymorph Form C shows no TGA weight loss.

Figure 4:
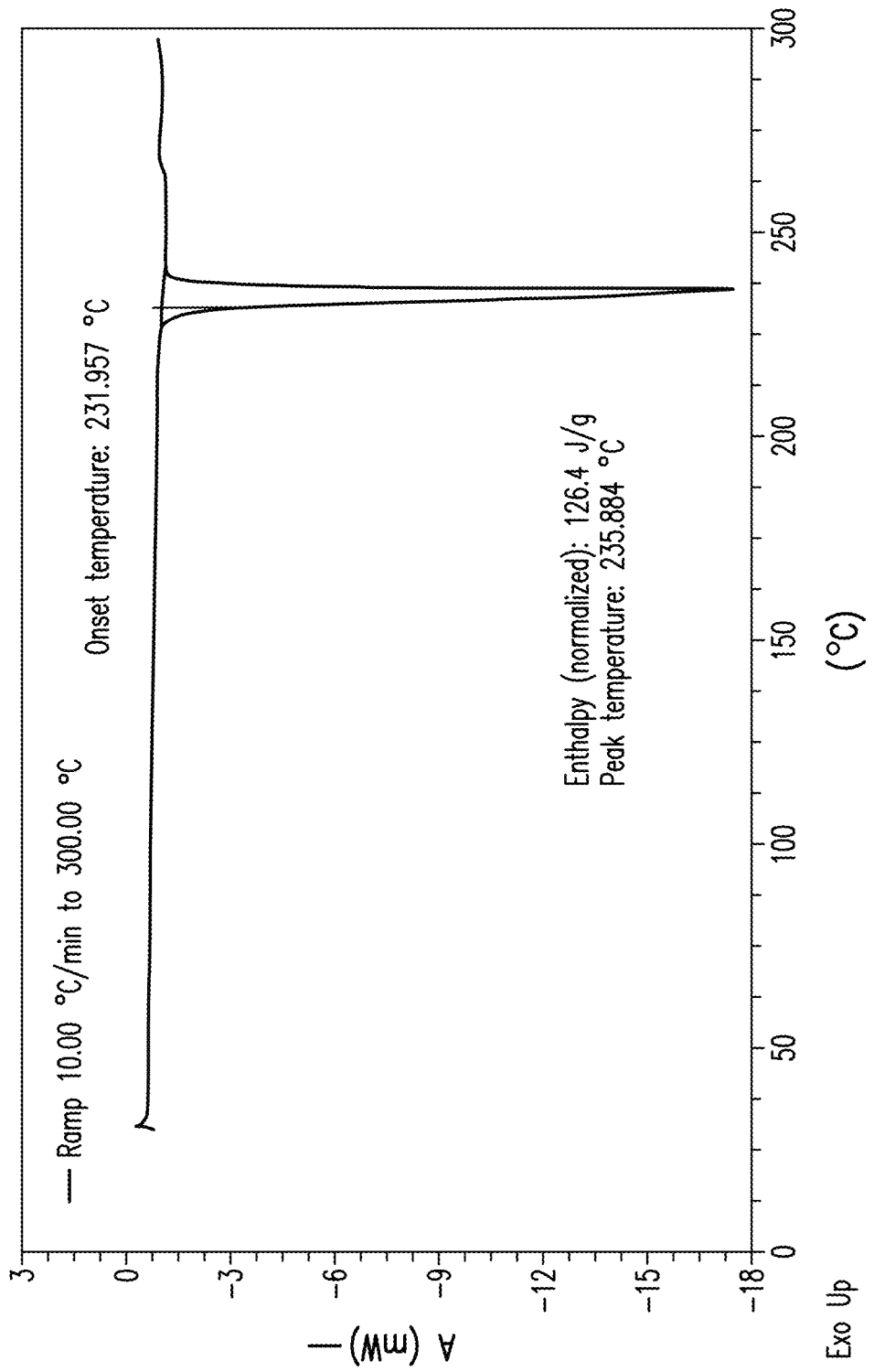
FIG. 4 depicts a DSC thermogram of polymorph Form C of 2-(4-chlorophenyl)-N-((2-(2,6-dioxopiperidin-3-yl)-1-oxoisoindolin-5-yl)methyl)-2,2-difluoroacetamide.

In one embodiment, polymorph Form C has a DSC thermogram corresponding substantially as depicted in FIG. 4. In certain embodiments, polymorph Form C is characterized by a DSC plot comprising melting event with an onset temperature of 232° C. and heat of fusion of 126 J/g.

Figure 5:
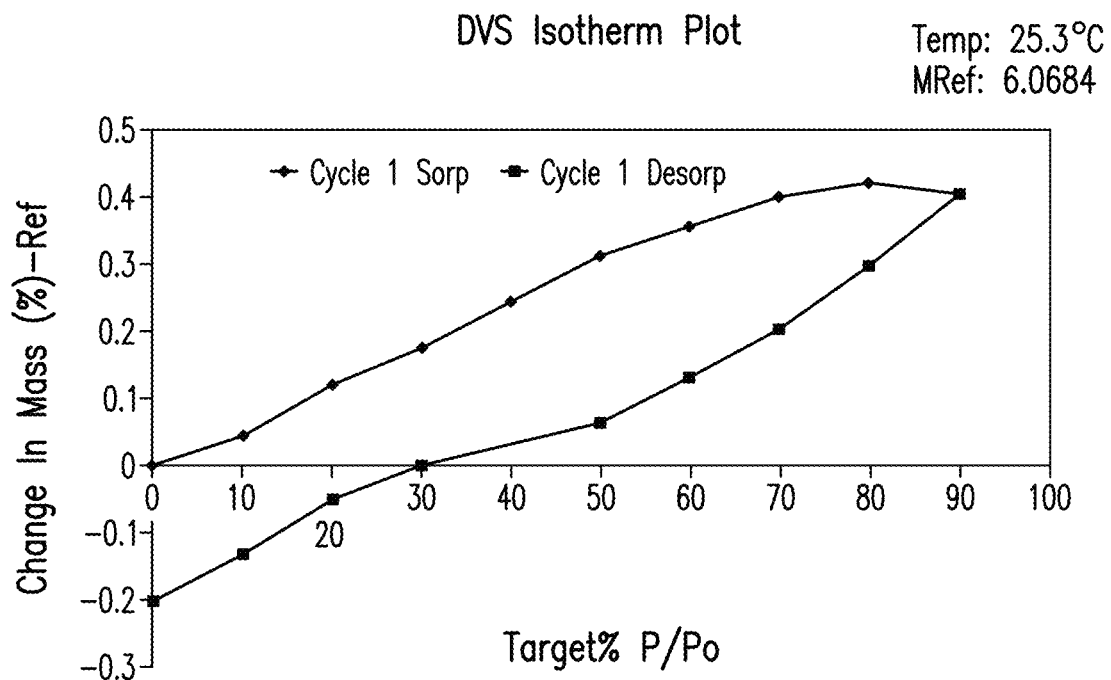
FIG. 5 provides a DVS isotherm plot of polymorph Form C of 2-(4-chlorophenyl)-N-((2-(2,6-dioxopiperidin-3-yl)-1-oxoisoindolin-5-yl)methyl)-2,2-difluoroacetamide.

In certain embodiments, polymorph Form C is characterized by dynamic vapor sorption analysis. A representative dynamic vapor sorption (DVS) isotherm plot is shown in FIG. 5. In certain embodiments, when the relative humidity ("RH") is increased from about 0% to about 90% RH, polymorph Form C exhibits about 0.6% w/w water uptake. In certain embodiments, polymorph Form C comprises less than 0.1% water as determined in a coulometric Karl Fischer (KF) titrator equipped with an oven sample processor set at 225° C.

Figure 6:
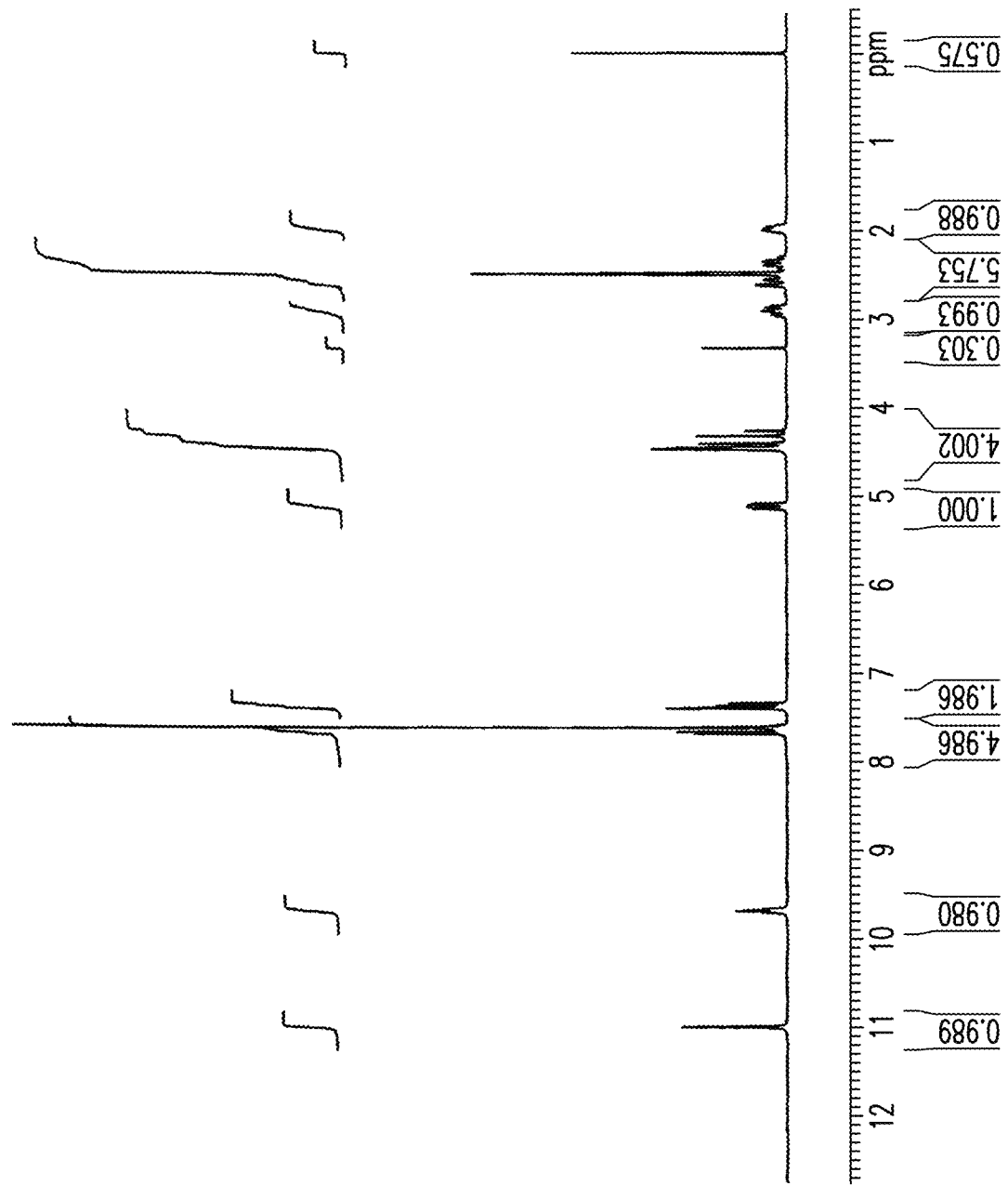
FIG. 6 provides a ¹H NMR spectrum of polymorph Form C of 2-(4-chlorophenyl)-N-((2-(2,6-dioxopiperidin-3-yl)-1-oxoisoindolin-5-yl)methyl)-2,2-difluoroacetamide.

In certain embodiments, polymorph Form C shows no significant degradation or residual solvent by $^1$H NMR (FIG. 6).

Figure 7:
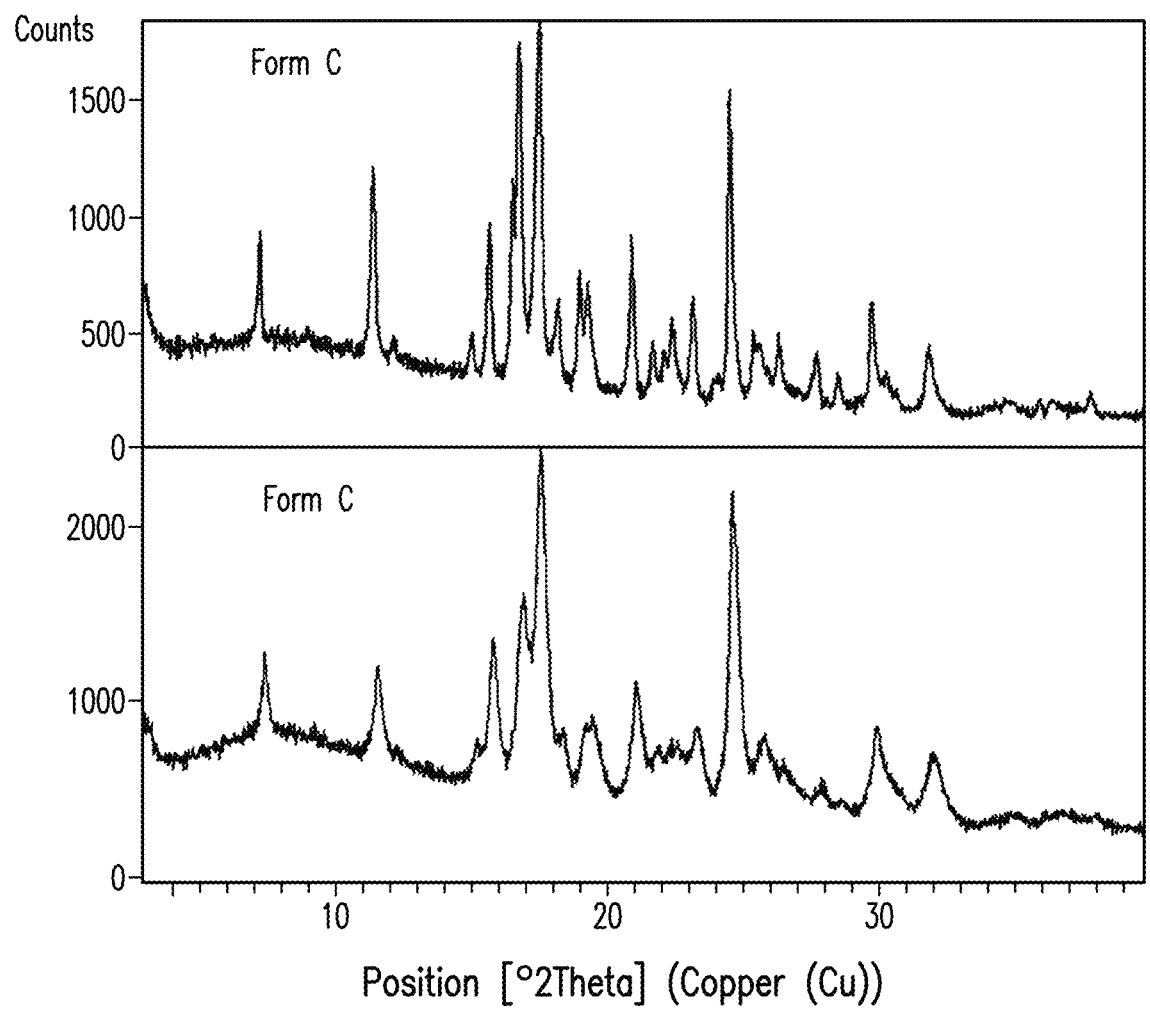
FIG. 7 depicts the comparison of the XRPD plots of polymorph Form C of 2-(4-chlorophenyl)-N-((2-(2,6-dioxopiperidin-3-yl)-1-oxoisoindolin-5-yl)methyl)-2,2-difluoroacetamide before and after application of pressure.

In certain embodiments, polymorph Form C of Compound 1 is characterized by its stability profile upon compression. In certain embodiments, Form C is stable, e.g., its XRPD pattern remains substantially unchanged with broader diffraction peaks, upon application of 2000-psi pressure for about 1 minute (FIG. 7).

In still another embodiment, the processes provided herein provide polymorph Form C that is substantially pure. In certain embodiments, the substantially pure polymorph Form C is substantially free of other solid forms, e.g., amorphous form. In certain embodiments, the purity of the substantially pure polymorph Form C is greater than 95%, greater than 96%, greater than 97%, greater than 98%, greater than 98.5%, greater than 99%, greater than 99.5%, greater than 99.8% or greater than 99.9%.

Processes

In one embodiment, provided herein is a process for preparing Compound 1

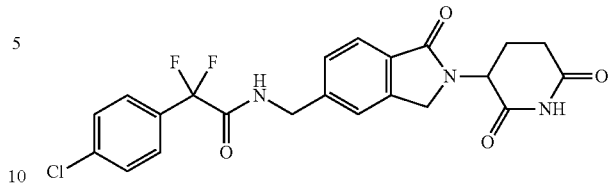

Compound 1 comprising contacting an acid salt of 3-(5-(aminomethyl)-1-oxoisoindolin-2-yl)piperidine-2,6-dione with 2-(4-chlorophenyl)-2,2-difluoroacetic acid (Compound M) with 2-(4-chlorophenyl)-2,2-difluoroacetic acid in the presence of thionyl chloride (SOCl$_2$), in a solvent under conditions suitable to provide Compound 1. In one embodiment, Compound M is the methanesulfonate, hydrochloride, sulfate, phosphate or acetate salt of 3-(5-(aminomethyl)-1-oxoisoindolin-2-yl)piperidine-2,6-dione with 2-(4-chlorophenyl)-2,2-difluoroacetic acid. In one embodiment, the solvent is N-methyl pyrrolidone (NMP). In one embodiment, Compound M is the methanesulfonate of of 3-(5-(aminomethyl)-1-oxoisoindolin-2-yl)piperidine-2,6-dione with 2-(4-chlorophenyl)-2,2-difluoroacetic acid.

In one embodiment, provided herein is a process for preparing Compound 1 comprising contacting Compound L1 with 2-(4-chlorophenyl)-2,2-difluoroacetic acid in the presence of a base and propylphosphonic anhydride (T3P), in a solvent, under conditions suitable to provide Compound 1. In one embodiment, the base is N-methylmorpholine (NMM). In one embodiment, the solvent is dimethylformamide (DMF).

In one embodiment, provided herein is a process for preparing Compound 1

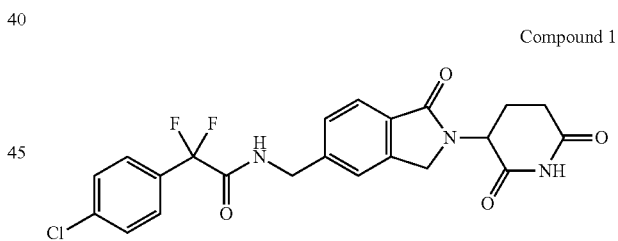

Compound 1 comprising contacting Compound L

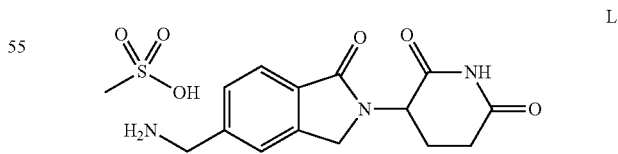

L with 2-(4-chlorophenyl)-2,2-difluoroacetic acid in the presence of SOCl$_2$, in a solvent under conditions suitable to provide Compound 1. In one embodiment, the solvent is NMP.

In one embodiment, provided herein is a process for preparing Compound 1

Compound 1

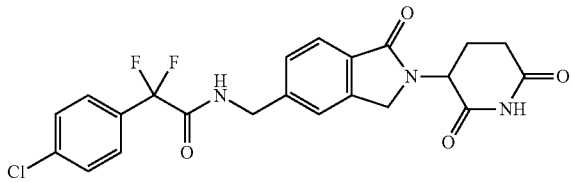

In one embodiment, provided herein is a process for preparing Compound L

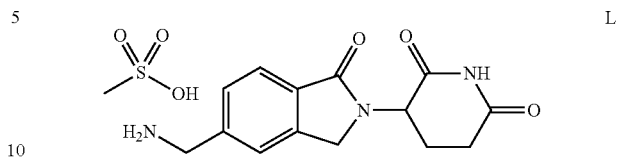

comprising contacting Compound L

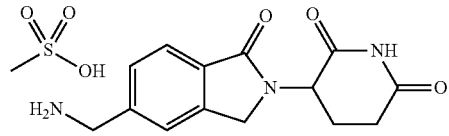

with 2-(4-chlorophenyl)-2,2-difluoroacetic acid in the presence of a base and T3P, in a solvent, under conditions suitable to provide Compound 1. In one embodiment, the base is NMM. In one embodiment, the solvent is DMF. In one embodiment, the contacting is performed at a temperature between about 35° C. to about 40° C. In one embodiment, the contacting is conducted for at least 12 hours.

In one embodiment, provided herein is a process for preparing Compound M comprising contacting Compound G

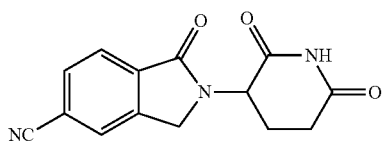

with a reducing agent, in a solvent, followed by contacting with an acid, under conditions suitable to provide Compound M. In one embodiment, the acid is methanesulfonic acid, hydrochloric acid, sulfuric acid, phosphoric acid, or acetic acid. In one embodiment, the reducing agent is 5% or 10% palladium on carbon. In one embodiment, the solvent comprises one or more solvents selected from NMP, 1-propanol, isopropyl alcohol, ethanol, tetrahydrofuran (THF) and optionally water. In one embodiment, the solvent comprises one or more of NMP, 1-propanol, isopropyl alcohol, ethanol and THF. In one embodiment, the solvent comprises isopropyl alcohol. In one embodiment, the solvent comprises isopropyl alcohol and water. In one embodiment, the solvent comprises isopropyl alcohol and water in a ratio of 1:4, 1:3 1:2 or 1:1 by volume. In one embodiment, the solvent comprises 1-propanol. In one embodiment, the solvent comprises 1-propanol and water in a ratio of 1:4, 1:3 1:2 or 1:1 by volume. In one embodiment, the solvent comprises NMP, 1-propanol and isopropyl alcohol. In one embodiment, the solvent comprises NMP, ethanol and THF.

comprising contacting Compound G

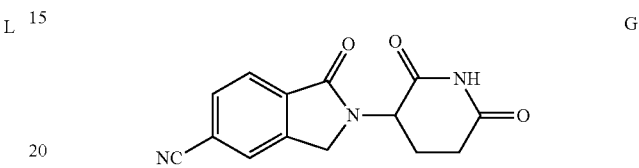

with a reducing agent, in a solvent, followed by contacting with methanesulfonic acid, under conditions suitable to provide Compound L. In one embodiment, the reducing agent is 5% or 10% palladium on carbon. In one embodiment, the solvent comprises 1-propanol. In one embodiment, the solvent comprises isopropyl alcohol. In one embodiment, the solvent comprises 1-propanol and water. In one embodiment, the solvent comprises isopropyl alcohol and water. In one embodiment, the solvent comprises isopropyl alcohol and water in a ratio of 1:4, 1:3 1:2 or 1:1 by volume. In one embodiment, the solvent comprises 1-propanol and water in a ratio of 1:4, 1:3 1:2 or 1:1 by volume. In one embodiment, the solvent is water, 1 propanol and isopropyl alcohol. In one embodiment, the solvent comprises NMP, 1-propanol, isopropyl alcohol, ethanol and THF. In one embodiment, the contacting with the reducing agent is conducted under 35 to 45 psi of $H_2$ pressure. In one embodiment, the contacting is performed at a temperature of about 25° to about 35° C. for at least 7 h.

In one embodiment, provided herein is a process for preparing 3-(5-(aminomethyl)-1-oxoisoindolin-2-yl)piperidine-2,6-dione with 2-(4-chlorophenyl)-2,2-difluoroacetic acid sulfate comprising contacting Compound G with a reducing agent, in a solvent, followed by contacting with sulfuric acid acid, under conditions suitable to provide 3-(5-(aminomethyl)-1-oxoisoindolin-2-yl)piperidine-2,6-dione with 2-(4-chlorophenyl)-2,2-difluoroacetic acid sulfurate. In one embodiment, the reducing agent is 10% palladium on carbon. In one embodiment, the solvent comprises NMP, 1-propanol and isopropyl alcohol.

In one embodiment, provided herein is a process for preparing 3-(5-(aminomethyl)-1-oxoisoindolin-2-yl)piperidine-2,6-dione with 2-(4-chlorophenyl)-2,2-difluoroacetic acid hydrochloride comprising contacting Compound G with a reducing agent, in a solvent, followed by contacting with hydrochloric acid acid, under conditions suitable to provide 3-(5-(aminomethyl)-1-oxoisoindolin-2-yl)piperidine-2,6-dione with 2-(4-chlorophenyl)-2,2-difluoroacetic acid hydrochloride. In one embodiment, the reducing agent is 5% or 10% palladium on carbon. In one embodiment, the solvent comprises NMP, ethanol and THF.

In one embodiment, provided herein is a process for preparing 3-(5-(aminomethyl)-1-oxoisoindolin-2-yl)piperidine-2,6-dione with 2-(4-chlorophenyl)-2,2-difluoroacetic acid phosphate comprising contacting Compound G with a reducing agent, in a solvent, followed by contacting with phosphoric acid, under conditions suitable to provide 3-(5-(aminomethyl)-1-oxoisoindolin-2-yl)piperidine-2,6-dione with 2-(4-chlorophenyl)-2,2-difluoroacetic acid phosphorate. In one embodiment, the reducing agent is 10% palladium on carbon. In one embodiment, the solvent comprises NMP and ethanol.

In one embodiment, provided herein is a process for preparing Compound G

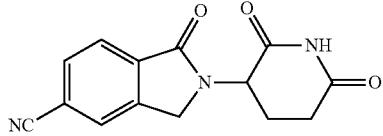

G comprising contacting Compound X

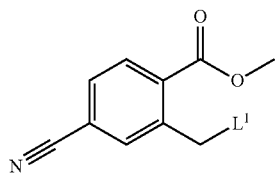

X wherein L¹ is a leaving group, with 3-aminopiperidine-2,6-dione hydrochloride in the presence of a salt, followed by a solvent and a base, under conditions suitable to provide Compound G. In one embodiment, L¹ is halogen or methanesulfonate. In one embodiment, L¹ is chloro or methanesulfonate. In one embodiment, the salt is potassium bromide or potassium iodide. In one embodiment, the base is N,N-diisopropylethylamine (DIPEA). In one embodiment, the solvent comprises acetonitrile and water. In one embodiment, the contacting is conducted at about 75° C. to about 80° C. for about 16 hours.

In one embodiment, provided herein is a process for preparing Compound G

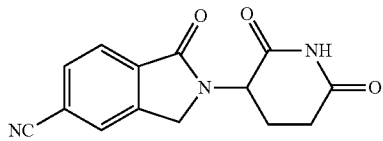

G comprising contacting Compound D

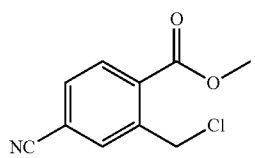

D with 3-aminopiperidine-2,6-dione hydrochloride in the presence of a salt, followed by a solvent and a base, under conditions suitable to provide Compound G. In one embodiment, the salt is potassium bromide or potassium iodide. In one embodiment, the base is DIPEA. In one embodiment, the solvent comprises acetonitrile and water. In one embodiment, the solvent comprises acetonitrile. In one embodiment, the contacting is conducted at about 75° C. to about 80° C. for about 16 hours.

In one embodiment, provided herein is a process for preparing Compound G

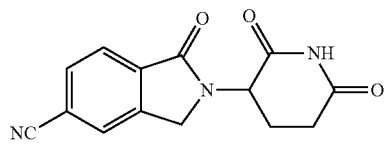

G comprising contacting Compound D1

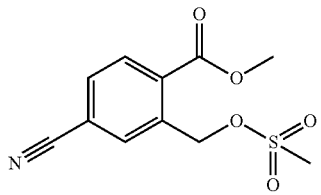

D1 with 3-aminopiperidine-2,6-dione hydrochloride in the presence of a salt, followed by a solvent and a base, under conditions suitable to provide Compound G. In one embodiment, the salt is potassium bromide or potassium iodide. In one embodiment, the base is DIPEA. In one embodiment, the solvent comprises acetonitrile and water. In one embodiment, the solvent comprises acetonitrile. In one embodiment, the contacting is conducted at about 75° C. to about 80° C. for about 16 hours.

In one embodiment, provided herein is a process for preparing Compound G

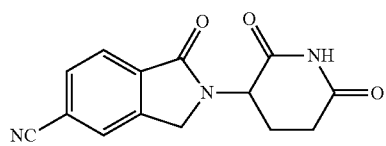

G comprising contacting Compound D

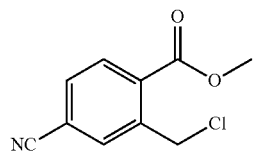

D with 3-aminopiperidine-2,6-dione hydrochloride in the presence of a base, followed by a solvent and a salt to obtain a reaction mixture, under conditions suitable to provide Compound G. In one embodiment, the salt is potassium bromide or potassium iodide. In one embodiment, the base is DIPEA. In one embodiment, the solvent comprises acetonitrile and water. In one embodiment, the solvent comprises acetonitrile. In one embodiment, the contacting is conducted at about 75° C. to about 80° C. for about 16 hours. In certain embodiments, the reaction mixture is contacted with acetic acid.

In one embodiment, provided herein is a process for preparing Compound G

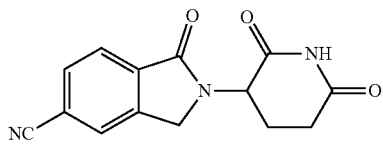

comprising contacting Compound D1

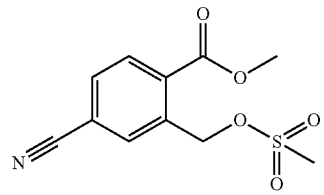

with 3-aminopiperidine-2,6-dione hydrochloride in the presence of a base, followed by a solvent and a salt to obtain a reaction mixture, under conditions suitable to provide Compound G. In one embodiment, the salt is potassium bromide or potassium iodide. In one embodiment, the base is DIPEA. In one embodiment, the solvent comprises acetonitrile and water. In one embodiment, the solvent comprises acetonitrile. In one embodiment, the contacting is conducted at about 75° C. to about 80° C. for about 16 hours. In certain embodiments, the reaction mixture is contacted with acetic acid.

In one embodiment, provided herein is a process for preparing Compound D

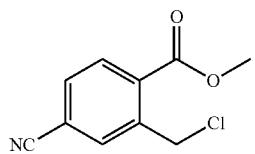

comprising contacting Compound A

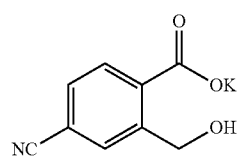

with 1) dimethyl sulfate in a solvent; 2) a base; 3) methanesulfonyl chloride (MsCl), and 4) lithium chloride (LiCl), under conditions suitable to provide Compound D. In one embodiment, the solvent is dimethylacetamide (DMAc). In one embodiment, the base is NMM. In one embodiment, the process comprises contacting Compound A with dimethyl sulfate in a solvent at about 10° C. for about 3 hours to obtain a slurry. In one embodiment, the slurry is contacted with a base, followed by methanesulfonyl chloride at about 10° C. to about 15° C. for between about 30 minutes and about 60 minutes. In one embodiment, the slurry is further contacted with lithium chloride.

In one embodiment, provided herein is a process for preparing Compound D1

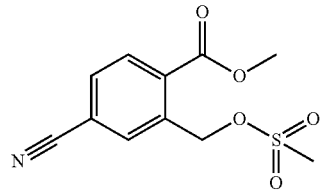

comprising contacting Compound A

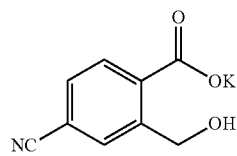

with 1) dimethyl sulfate in a solvent; 2) a base; and 3) methanesulfonic anhydride (Ms$_2$O), under conditions suitable to provide Compound D1. In one embodiment, the solvent is DMAc. In one embodiment, the base is NMM. In one embodiment, the process comprises contacting Compound A in a solvent at about 20-25° C. with dimethyl sulfate to obtain a slurry. In one embodiment, the slurry is contacted with a base, followed by Ms$_2$O in DMAc at about 20-25° C.

In one embodiment, provided herein is a process for preparing Compound A

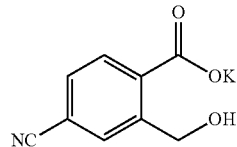

comprising contacting 1-oxo-1,3-dihydroisobenzofuran-5-carbonitrile

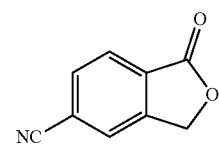 [SMILES: N#Cc1ccc2c(c1)COC2=O]

with a base, in a solvent, under conditions suitable to provide Compound A. In one embodiment, the base is potassium hydroxide. In one embodiment, the solvent comprises isopropyl alcohol and water. In one embodiment, the contacting is conducted at about 35° C. to about 40° C. for about 2 hours.

In one embodiment, provided herein is a process for preparing Compound 1

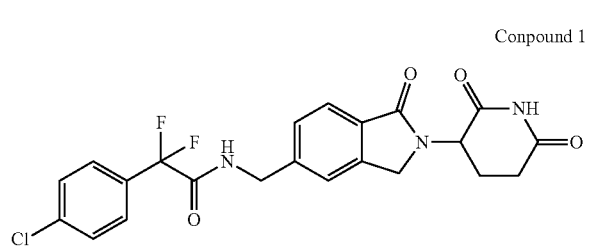 [SMILES: O=C1CCC(N2Cc3cc(CNC(=O)C(F)(F)c4ccc(Cl)cc4)ccc3C2=O)C(=O)N1]
Conpound 1 comprising contacting Compound L

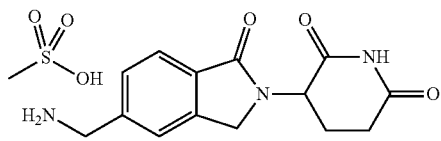
L with 2-(4-chlorophenyl)-2,2-difluoroacetic acid in the presence of NMP and SOCl$_2$, under conditions suitable to provide Compound 1.

In one embodiment, provided herein is a process for preparing Compound 1

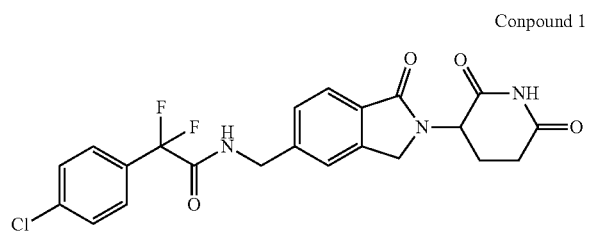
Conpound 1 comprising contacting Compound L

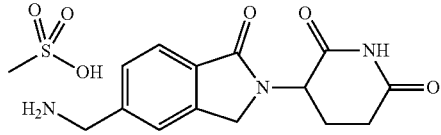
L with 2-(4-chlorophenyl)-2,2-difluoroacetic acid in the presence of DMF, NMM and T3P, under conditions suitable to provide Compound 1.

In one embodiment, provided herein is a process for preparing Compound 1

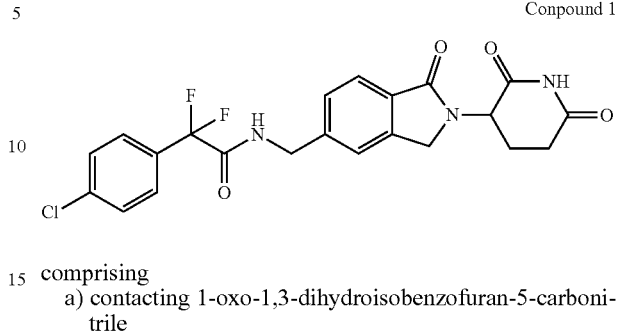
Conpound 1 comprising
a) contacting 1-oxo-1,3-dihydroisobenzofuran-5-carbonitrile

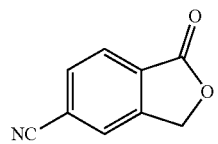 [SMILES: N#Cc1ccc2c(c1)COC2=O]

with a first base in a first solvent, under conditions suitable to provide Compound A

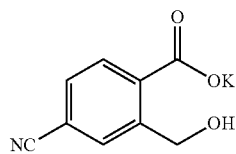
A b) contacting Compound A with 1) dimethyl sulfate in a second solvent, 2) a second base, 3) methanesulfonyl chloride, and 4) lithium chloride, under conditions suitable to provide Compound D

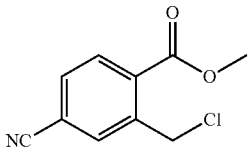
D c) contacting Compound D with i) 3-aminopiperidine-2,6-dione hydrochloride in the presence of a salt, followed by ii) a third solvent and iii) a third base, under conditions suitable to provide Compound G,

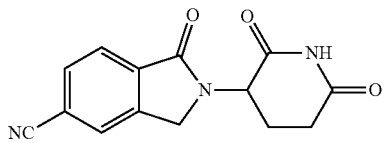
G d) contacting Compound G with a reducing agent in a fourth solvent followed by methanesulfonic acid, under conditions suitable to provide Compound L

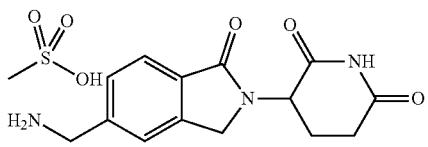

and e) contacting Compound L with 2-(4-chlorophenyl)-2,2-difluoroacetic acid in the presence of SOCl₂ in a fifth solvent, under conditions suitable to provide 2-(4-chlorophenyl)-N-((2-(2,6-dioxopiperidin-3-yl)-1-oxoisoindolin-5-yl)methyl)-2,2-difluoroacetamide.

In one embodiment, the first base is potassium hydroxide. In one embodiment, the first solvent is isopropyl alcohol. In one embodiment, the second base is NMM. In one embodiment, the second solvent is DMAc. In one embodiment, the third base is DIPEA. In one embodiment, the third solvent is acetonitrile and water. In one embodiment, the third solvent is acetonitrile. In one embodiment, the fourth solvent is propanol and water. In one embodiment, the fifth solvent is NMP.

In one embodiment, provided herein is a process for preparing Compound 1

Compound 1

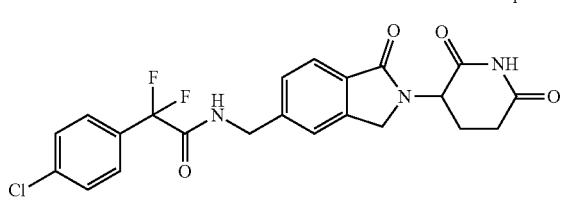

comprising a) contacting 1-oxo-1,3-dihydroisobenzofuran-5-carbonitrile

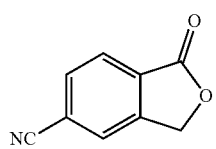 [SMILES: N#Cc1ccc2c(c1)COC2=O]

with a first base in a first solvent, under conditions suitable to provide Compound A

A

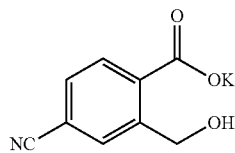

b) contacting Compound A with 1) dimethyl sulfate in a second solvent, 2) a second base, 3) methanesulfonyl chloride, and 4) lithium chloride, under conditions suitable to provide Compound D

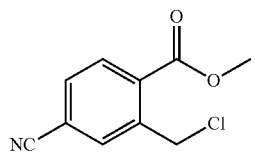

c) contacting Compound D with i) 3-aminopiperidine-2,6-dione hydrochloride in the presence of a salt, followed by ii) a third solvent and iii) a third base, under conditions suitable to provide Compound G,

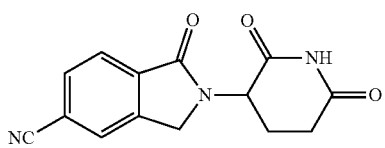

d) contacting Compound G with a reducing agent in a fourth solvent followed by methanesulfonic acid, under conditions suitable to provide Compound L

L

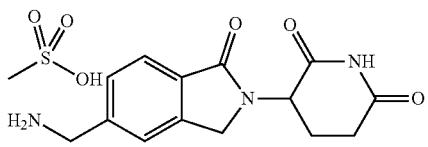

and e) contacting Compound L with 2-(4-chlorophenyl)-2,2-difluoroacetic acid in the presence of T3P in a fifth solvent and a fourth base, under conditions suitable to provide 2-(4-chlorophenyl)-N-((2-(2,6-dioxopiperidin-3-yl)-1-oxoisoindolin-5-yl)methyl)-2,2-difluoroacetamide.

In one embodiment, the first base is potassium hydroxide. In one embodiment, the first solvent is isopropyl alcohol. In one embodiment, the second base is NMM. In one embodiment, the second solvent is DMAc. In one embodiment, the third base is DIPEA. In one embodiment, the third solvent is acetonitrile and water. In one embodiment, the third solvent is acetonitrile. In one embodiment, the fourth solvent is propanol, water and isopropyl alcohol. In one embodiment, the fifth solvent is DMF. In one embodiment, the fourth base is NMM.

In one embodiment, provided herein is a process for preparing Compound 1

Compound 1

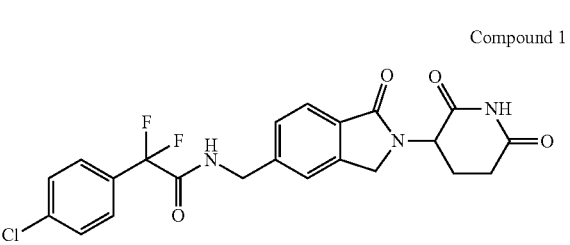 [SMILES: O=C1CCC(N2Cc3cc(CNC(=O)C(F)(F)c4ccc(Cl)cc4)ccc3C2=O)C(=O)N1]

comprising a) contacting 1-oxo-1,3-dihydroisobenzofuran-5-carbonitrile

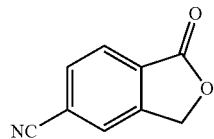

with a potassium hydroxide in isopropyl alcohol, under conditions suitable to provide Compound A

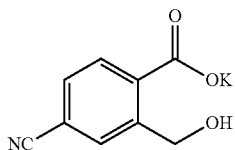

A b) contacting Compound A with 1) dimethyl sulfate in DMAc, 2) NMM, 3) methanesulfonyl chloride, and 4) lithium chloride, under conditions suitable to provide Compound D

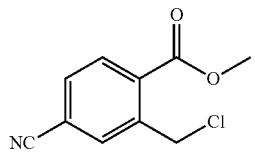

D c) contacting Compound D with i) 3-aminopiperidine-2,6-dione hydrochloride in the presence of a potassium bromide or potassium iodide, followed by ii) acetonitrile and water or acetonitrile only and iii) DIPEA, under conditions suitable to provide Compound G,

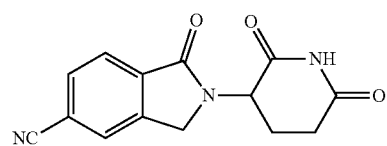

G d) contacting Compound G with a reducing agent in water and propanol followed by methanesulfonic acid, under conditions suitable to provide Compound L

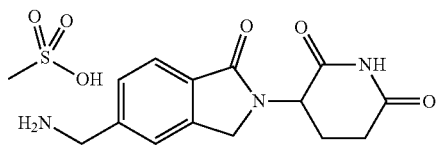

L and e) contacting Compound L with 2-(4-chlorophenyl)-2,2-difluoroacetic acid in the presence of SOCl$_2$ in NMP, under conditions suitable to provide 2-(4-chlorophenyl)-N-((2-(2,6-dioxopiperidin-3-yl)-1-oxoisoindolin-5-yl)methyl)-2,2-difluoroacetamide.

In one embodiment, provided herein is a process for preparing Compound 1

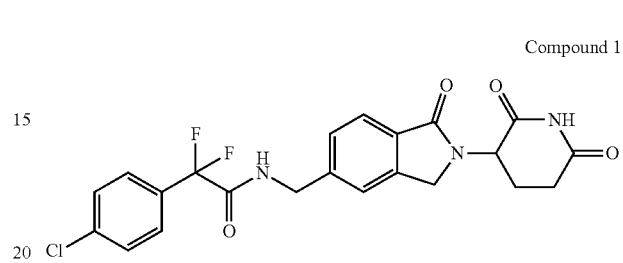

Compound 1 comprising a) contacting 1-oxo-1,3-dihydroisobenzofuran-5-carbonitrile

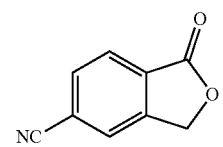 [SMILES: N#Cc1ccc2c(c1)COC2=O]

with potassium hydroxide in isopropyl alcohol, under conditions suitable to provide Compound A

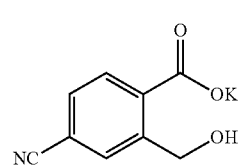

A b) contacting Compound A with 1) dimethyl sulfate in DMAc, 2) NMM, 3) methanesulfonyl chloride, and 4) lithium chloride, under conditions suitable to provide Compound D

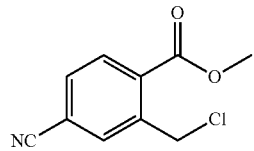

D c) contacting Compound D with i) 3-aminopiperidine-2,6-dione hydrochloride in the presence of potassium bromide or potassium iodide, followed by ii) a solvent comprising acetonitrile and water, iii) DIPEA, and iv) acetic acid, under conditions suitable to provide Compound G,

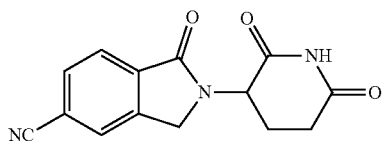

G d) contacting Compound G with 10% wt Pd/C, methanesulfonic acid, and a solvent comprising water and 1-propanol, under conditions suitable to provide Compound L

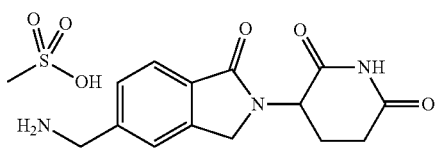

L and e) contacting Compound L with 2-(4-chlorophenyl)-2,2-difluoroacetic acid in the presence of DMF, NMM and T3P, under conditions suitable to provide Compound 1.

In one embodiment, provided herein is a process for preparing Compound 1

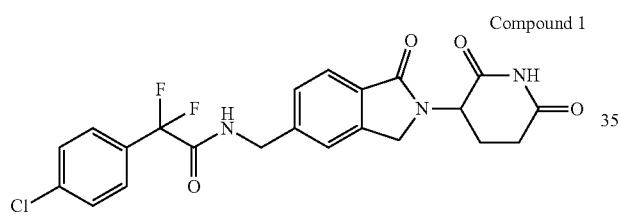

Compound 1 comprising a) contacting 1-oxo-1,3-dihydroisobenzofuran-5-carbonitrile

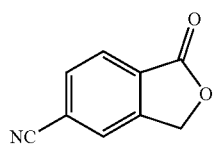 [SMILES: N#Cc1ccc2c(c1)COC2=O]

with potassium hydroxide in isopropyl alcohol, under conditions suitable to provide Compound A

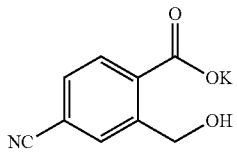

A b) contacting Compound A with 1) dimethyl sulfate in DMAc, 2) NMM, 3) methanesulfonyl chloride, and 4) lithium chloride, under conditions suitable to provide Compound D

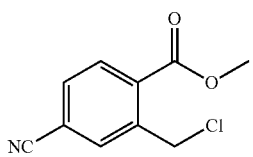

D c) contacting Compound D with i) 3-aminopiperidine-2,6-dione hydrochloride in the presence of potassium bromide or potassium iodide, followed by ii) a solvent comprising acetonitrile and water, iii) DIPEA, and iv) acetic acid, under conditions suitable to provide Compound G,

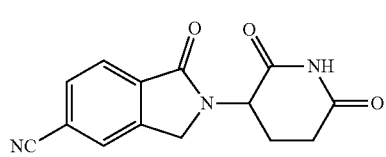

G d) contacting Compound G with 10% wt Pd/C, methanesulfonic acid, and a solvent comprising water, 1-propanol and isopropyl alcohol, under conditions suitable to provide Compound L

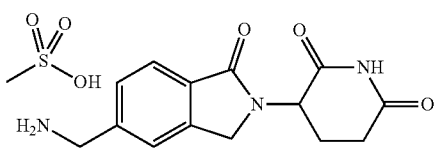

L and e) contacting Compound L with 2-(4-chlorophenyl)-2,2-difluoroacetic acid in the presence of DMF, NMM and T3P, under conditions suitable to provide Compound 1.

In one embodiment, provided herein is a process for preparing polymorph Form C of Compound 1 comprising contacting Compound 1 obtained in the processes provided herein with formic acid and water at about 55° C. to about 65° C. for at least 16 hours to obtain polymorph Form C of Compound 1. In one embodiment, the process further comprises cooling the reaction mixture to between about 15° C. and about 25° C.

In one embodiment, provided herein is a process for preparing polymorph Form C of Compound 1 comprising contacting Compound 1 obtained in the processes provided herein with acetone to obtain a mixture, heating the mixture under nitrogen to between about 70° C. and about 75° C. with agitation, cooling the mixture to room temperature, and filtering the mixture to obtain a cake. The cake is washed with acetone and dried to obtain Form C of Compound 1.

In one embodiment, provided herein is a process for preparing polymorph Form C of Compound 1 comprising a) contacting 1-oxo-1,3-dihydroisobenzofuran-5-carbonitrile

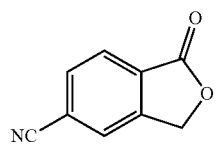 [SMILES: N#Cc1ccc2c(c1)COC2=O]

with potassium hydroxide in isopropyl alcohol, under conditions suitable to provide Compound A

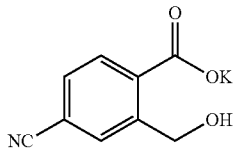

A b) contacting Compound A with 1) dimethyl sulfate in DMAc, 2) NMM, 3) methanesulfonyl chloride, and 4) lithium chloride, under conditions suitable to provide Compound D

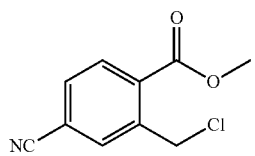

D c) contacting Compound D with i) 3-aminopiperidine-2,6-dione hydrochloride in the presence of potassium bromide or potassium iodide, followed by ii) a solvent comprising acetonitrile, water and acetic acid, and iii) DIPEA, under conditions suitable to provide Compound G,

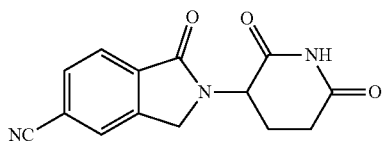

G d) contacting Compound G with 10% wt Pd/C, methanesulfonic acid, and a solvent comprising water and 1-propanol, under conditions suitable to provide Compound L

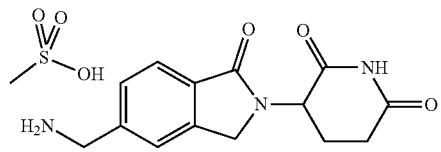

L e) contacting Compound L with 2-(4-chlorophenyl)-2,2-difluoroacetic acid in the presence of DMF, NMM and T3P, under conditions suitable to provide Compound 1, and f) contacting Compound 1 with formic acid and water to obtain polymorph Form C of Compound 1.

In one embodiment, provided herein is a process for preparing polymorph Form C of Compound 1 comprising a) contacting 1-oxo-1,3-dihydroisobenzofuran-5-carbonitrile

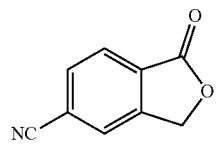 [SMILES: N#Cc1ccc2c(c1)COC2=O]

with potassium hydroxide in isopropyl alcohol, under conditions suitable to provide Compound A

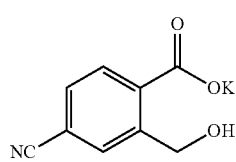

A b) contacting Compound A with 1) dimethyl sulfate in DMAc, 2) NMM, 3) methanesulfonyl chloride, and 4) lithium chloride, under conditions suitable to provide Compound D

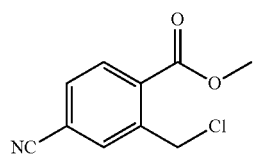

D c) contacting Compound D with i) 3-aminopiperidine-2,6-dione hydrochloride in the presence of potassium bromide or potassium iodide, followed by ii) a solvent comprising acetonitrile and water, iii) DIPEA, and iv) acetic acid under conditions suitable to provide Compound G,

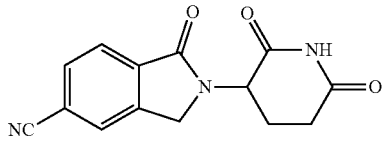

G d) contacting Compound G with 10% wt Pd/C, methanesulfonic acid, and a solvent comprising water and 1-propanol, under conditions suitable to provide Compound L

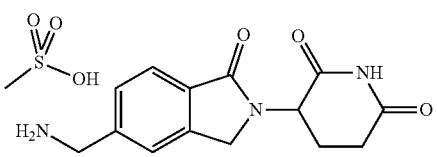
L e) contacting Compound L with 2-(4-chlorophenyl)-2,2-difluoroacetic acid in the presence of DMF, NMM and T3P, under conditions suitable to provide Compound 1, and f) contacting Compound 1 with formic acid and water to obtain polymorph Form C of Compound 1.

In one embodiment, provided herein is a process for preparing polymorph Form C of Compound 1 comprising a) contacting 1-oxo-1,3-dihydroisobenzofuran-5-carbonitrile

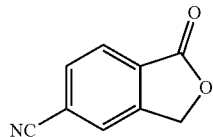

with potassium hydroxide in isopropyl alcohol, under conditions suitable to provide Compound A

A b) contacting Compound A with 1) dimethyl sulfate in DMAc, 2) NMM, 3) methanesulfonyl chloride, and 4) lithium chloride, under conditions suitable to provide Compound D

D c) contacting Compound D with i) 3-aminopiperidine-2,6-dione hydrochloride in the presence of potassium bromide or potassium iodide, followed by ii) a solvent comprising acetonitrile and water, iii) DIPEA, and iv) acetic acid, under conditions suitable to provide Compound G,

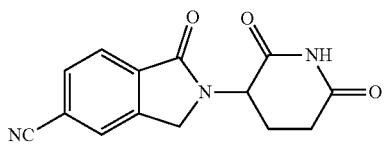
G d) contacting Compound G with 10% wt Pd/C, methanesulfonic acid, and a solvent comprising water, 1-propanol and isopropyl alcohol, under conditions suitable to provide Compound L

L and e) contacting Compound L with 2-(4-chlorophenyl)-2,2-difluoroacetic acid in the presence of DMF, NMM and T3P, under conditions suitable to provide Compound 1, and f) contacting Compound 1 with formic acid and water at about 55° C. to about 65° C. for at least about 16 hours to obtain polymorph Form C of Compound 1.

In one embodiment, the processes herein provide improved yield of polymorph Form C of Compound 1 as compared to the processes in the art. In one embodiment, the processes herein provide about 2 to about 9 fold improved yield of polymorph Form C of Compound 1 as compared to the processes in the art. In one embodiment, the processes herein provide over 2, 3, 4, 5, 6, 7, 8 or 9 fold improved yield of polymorph Form C of Compound 1 as compared to the processes in the art. In one embodiment, the processes herein provide about 9 fold improved yield of polymorph Form C of Compound 1 as compared to the processes in the art.

In one embodiment, the processes herein provide polymorph Form C of Compound 1 in overall yield of about 40% or more. In one embodiment, the processes herein provide polymorph Form C of Compound 1 in overall yield of about 45% or more. In one embodiment, the processes herein provide polymorph Form C of Compound 1 in overall yield of about 50% or more. In one embodiment, the processes herein provide polymorph Form C of Compound 1 in overall yield of about 45% to about 55%. In one embodiment, the processes herein provide polymorph Form C of Compound 1 in overall yield of about 53%.

In one embodiment, the processes herein provide an improvement in yield of Compound 1 as compared to the processes known in the art. In one embodiment, the yield of Compound 1 in the processes provided herein is about 50% to about 55%, whereas the yield in the processes known in the art is about 6%. In one embodiment, the yield of Compound 1 in the processes provided herein is about 53%.

In one embodiment, the processes herein provide polymorph Form C of Compound 1 having a purity of about 99% to about 100%. In one embodiment, the processes herein provide polymorph Form C of Compound 1 having a purity of about 99.9%. In one embodiment, the processes herein provide polymorph Form C of Compound 1 having no detectable impurities.

In one embodiment, the improvement in the processes provided herein as compared to the processes known in the art includes use of inexpensive starting material, for example 5-cyano phthalide. In one embodiment, the improvement in the processes provided herein as compared to the processes known in the art includes improved safety. In one embodiment, the process provided herein eliminates the potentially unsafe radical reaction employing N-bromosuccinimide. In one embodiment, the improvement in the processes provided herein as compared to the processes known in the art includes improved efficiency. In one embodiment, the processes provided herein result in improved yields. In one embodiment, the processed provided here are simplified, for example, no silica gel chromatography is used throughout the entire process. In one embodiment, the improvement in the processes provided herein as compared to the processes known in the art includes less toxic and environmentally friendly reaction conditions. In one embodiment, the processes provided herein eliminate the highly toxic KCN reagent in the previously reported process, thereby avoiding waste containing toxic cyanide.

In certain embodiments, provided herein are chemical intermediates useful in the methods provided herein. In certain embodiments, provided herein are chemical intermediates useful in the synthesis of Compound 1.

In one embodiment, provided herein is Compound A

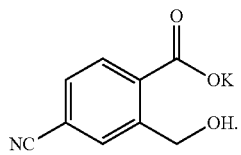

A

In one embodiment, provided herein is Compound X

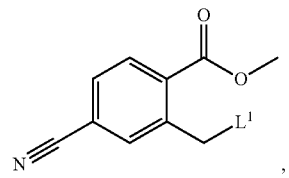

X where L¹ is a leaving group. In one embodiment, L¹ is halogen or methanesulfonate. In one embodiment, L¹ is chloro or methanesulfonate.

In one embodiment, provided herein is Compound D

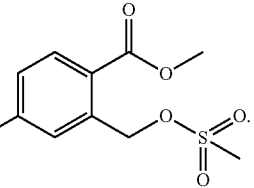

D

In one embodiment, provided herein is Compound D1

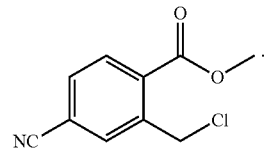

D1

Synthetic Schemes

In certain embodiments, Compound 1 is prepared as outlined in schemes 1 or 2 shown below, as well as in the examples set forth in the Example section. It should be noted that one skilled in the art can modify the procedures set forth in the illustrative schemes and examples to arrive at the desired product.

Scheme 1

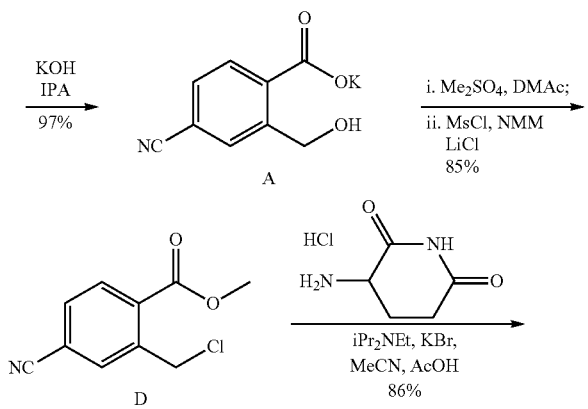

33 34
-continued
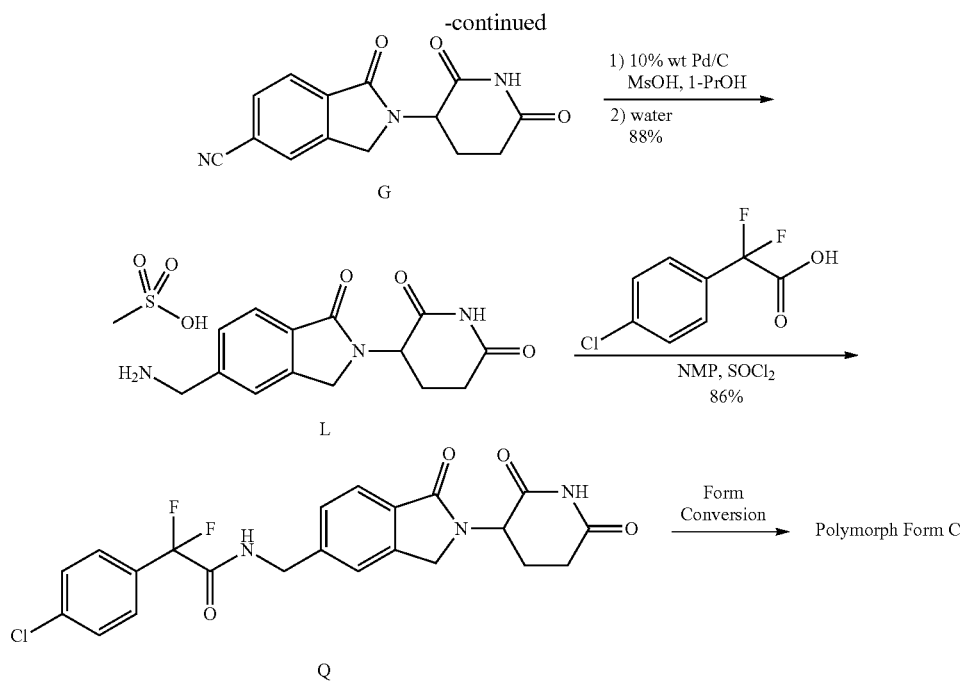
Scheme 2
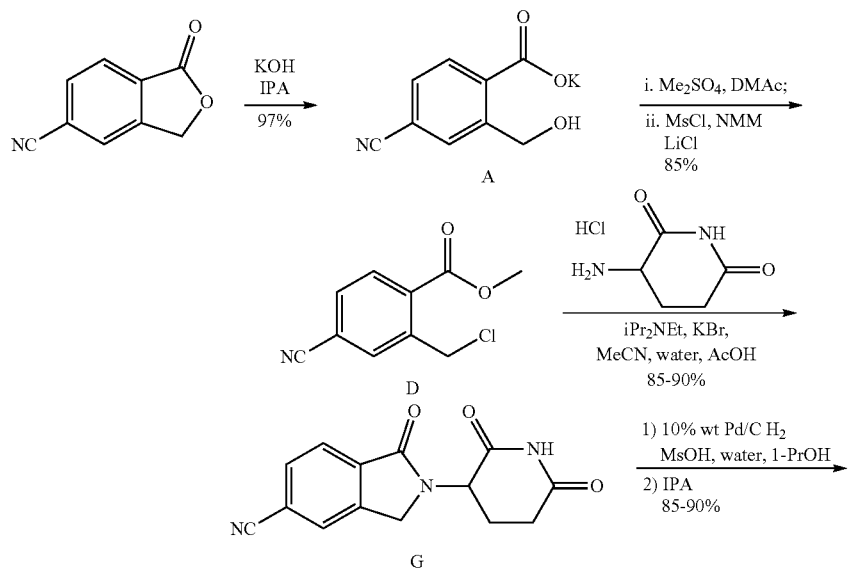
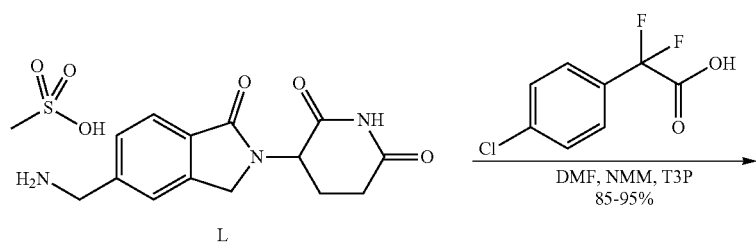

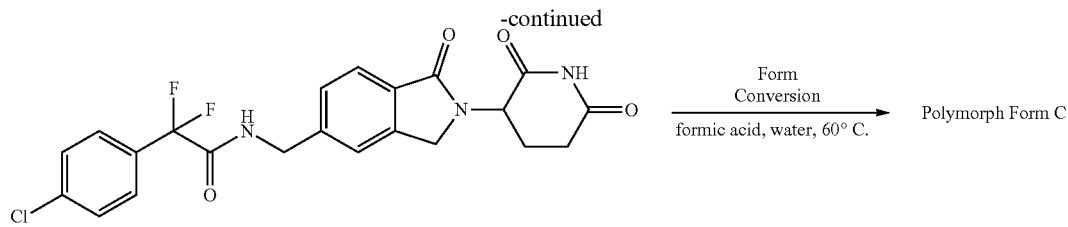

Methods of Use

Compound 1 described herein has utility in methods of treating cancer. Described herein is Compound 1 for use in methods of treating cancer. Exemplary methods of treating cancer comprising administering Compound 1 are described in US Publication No. US 2019/003018 A1.

In the following, embodiments are provided herein that include all possible combinations of the particular embodiments set forth herein.

In one embodiment, provided herein are methods for inhibition of disease progression, inhibition of tumor growth, reduction of primary tumor, relief of tumor-related symptoms, inhibition of tumor secreted factors, delaying appearance of primary or secondary tumors, slowing development of primary or secondary tumors, decreasing occurrence of primary or secondary tumors, slowing or decreasing severity of secondary effects of disease, arresting tumor growth and regression of tumors, increasing time to progression, increasing progression free survival, increasing overall survival in a cancer patient, or one or more thereof, comprising administering an effective amount of Compound 1 to the patient. In one embodiment, provided herein is Compound 1 for use in methods for inhibition of disease progression, inhibition of tumor growth, reduction of primary tumor, relief of tumor-related symptoms, inhibition of tumor secreted factors, delaying appearance of primary or secondary tumors, slowing development of primary or secondary tumors, decreasing occurrence of primary or secondary tumors, slowing or decreasing severity of secondary effects of disease, arresting tumor growth and regression of tumors, increasing time to progression, increasing progression free survival, increasing overall survival in a cancer patient, or one or more thereof, comprising administering an effective amount of Compound 1 to the patient.

Also provided herein is Compound 1 for use in methods of treating any disease provided herein related to by Compound 1.

In certain embodiments, the cancer is a solid tumor or a hematological cancer. In certain embodiments, the cancer is interleukin-3 (IL-3) independent. In certain embodiments, the cancer is a solid tumor. In certain embodiments, the solid tumor is metastatic. In certain embodiments, the solid tumor is drug-resistant.

In certain embodiments, cancer refers to a disease of skin tissues, organs, blood, and vessels. In certain embodiments, the cancer is a solid tumor, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, colorectal cancer, including stage 3 and stage 4, unresectable colorectal carcinoma, metastatic hepatocellular carcinoma, Kaposi's sarcoma, karyotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, carcinoma, including papillary thyroid carcinoma, follicular thyroid carcinoma, and medullary thyroid carcinoma, and leiomyoma.

In certain embodiments, the cancer is leukemia, lymphoma, Hodgkin's disease or myeloma. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders or myeloproliferative neoplasm (MPN), chronic myelogenous leukemia (CML), myelodysplastic syndrome (MDS), human lymphotropic virus-type 1 (HTLV 1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma. In one embodiment, the hematological malignancy is AML. In another embodiment, the hematological malignancy is MDS.

In one embodiment, provided herein are methods of treating cancer comprising administering Compound 1 in combination with one or more second active agents, and optionally in combination with radiation therapy, blood transfusions, or surgery. In one embodiment, provided herein is Compound 1 for use in methods of treating cancer comprising administering Compound 1 in combination with one or more second active agents, and optionally in combination with radiation therapy, blood transfusions, or surgery. In one embodiment, the second active agent is an anti-cancer agent. In one embodiment, the second active agent is selected from a JAK inhibitor, FLT3 inhibitor, mTOR inhibitor, spliceosome inhibitor, BET inhibitor, SMG1 inhibitor, ERK inhibitors, LSD1 inhibitor, BH3 mimetic, topoisomerase inhibitor, and RTK inhibitor.

Pharmaceutical Compositions and Routes of Administration

Compound 1 prepared by the processes provided herein is useful for the preparation of pharmaceutical compositions, comprising an effective amount of Compound 1 and a pharmaceutically acceptable excipient, carrier or vehicle. In some embodiments, the pharmaceutical composition described herein are suitable for oral, parenteral, mucosal, transdermal or topical administration.

EXAMPLES

The following abbreviations were used in descriptions and examples:
ACN or MeCN: Acetonitrile
AcOH: Acetic acid
AIBN: Azo-isobutyronitrile
DAST: Diethylaminosulfur trifluoride
DIEA or DIPEA or iPr$_2$NEt: N,N-diisopropylethylamine
DMA or DMAc: Dimethylacetamide
DMF: Dimethylformamide
DMS: Dimethyl sulfate
DPPF: 1,1' Bis(diphenylphosphino)ferrocene
EDC: 1-Ethyl-3-(3-dimethylaminopropyl)carbodiimide
HOBt: Hydroxybenzotriazole
HPLC: High performance liquid chromatography
IPA or i-PrOH: Isopropyl alcohol
MeOH: Methanol
Me$_2$SO$_4$: Dimethyl sulfate
MsCl: Methanesulfonyl chloride
Ms$_2$O: Methanesulfonic anhydride
MsOH: Methanesulfonic acid
NBS: N-Bromosuccinimide
NMM: N-methyl morpholine
Pd$_2$(dba)$_3$: Tris(dibenzylideneacetone)dipalladium(0)
1-PrOH: 1-Propyl alcohol
T3P: Propylphosphonic anhydride
TEA: Triethylamine
RT: Room temperature
Zn(OAC)$_2$: Zinc acetate The following Examples are presented by way of illustration, not limitation.

Example 1 (Reference Example)

Synthesis of 2-(4-chlorophenyl)-N-((2-(2,6-dioxopiperidin-3-yl)-1-oxoisoindolin-5-yl)methyl)-2,2-difluoroacetamide The title compound was prepared as described in U.S. Pat. No. 9,499,514 B2, according to the following reaction scheme

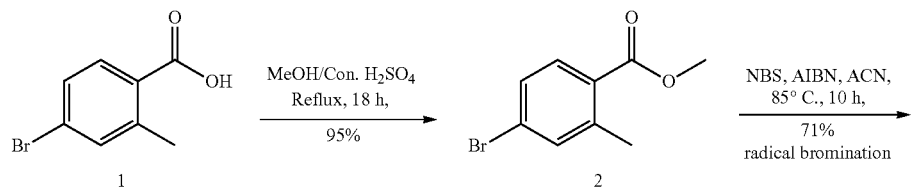

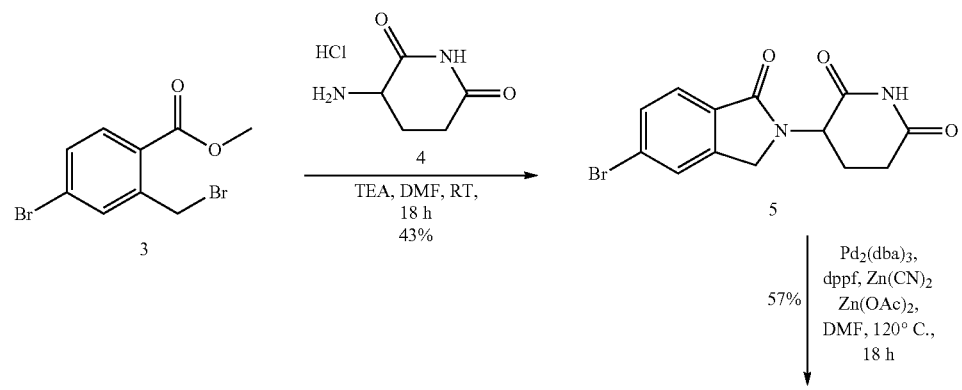

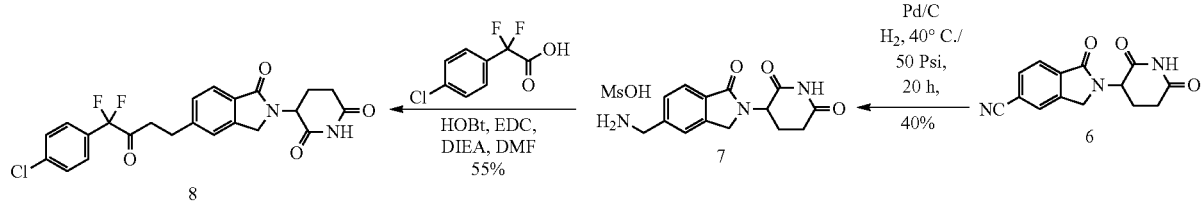
Overall yield of the title compound in this process is about 6.4%.
Example 2
Synthesis of 2-(4-chlorophenyl)-N-((2-(2,6-dioxopiperidin-3-yl)-1-oxoisoindolin-5-yl)methyl)-2,2-difluoroacetamide
The title compound was prepared according to the following reaction scheme
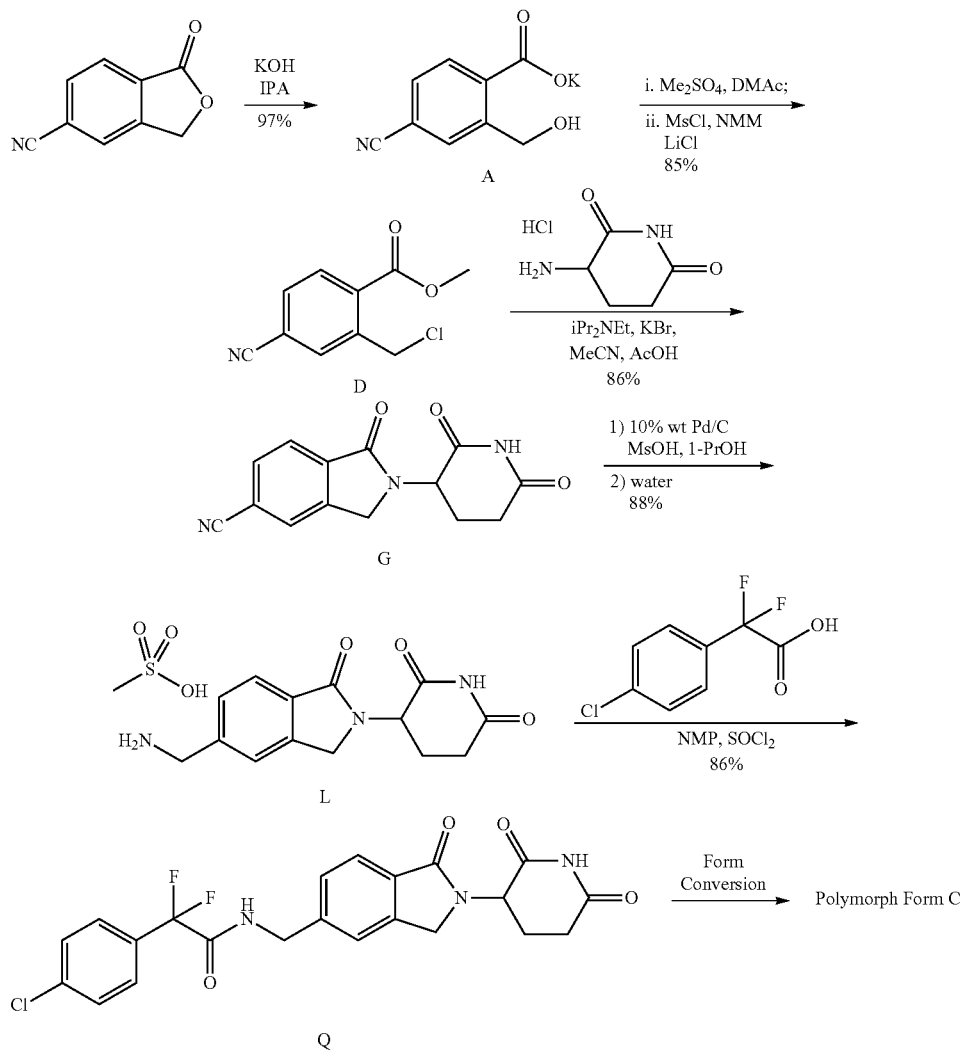

Overall yield of the title compound in this process is about 53%. The HPLC purity of polymorph Form C is obtained in this process is >99.9%. No detectable impurities were found in the final product.

Example 3

Synthesis of 2-(4-chlorophenyl)-N-((2-(2,6-dioxopiperidin-3-yl)-1-oxoisoindolin-5-yl)methyl)-2,2-difluoroacetamide The title compound was prepared according to the following reaction scheme

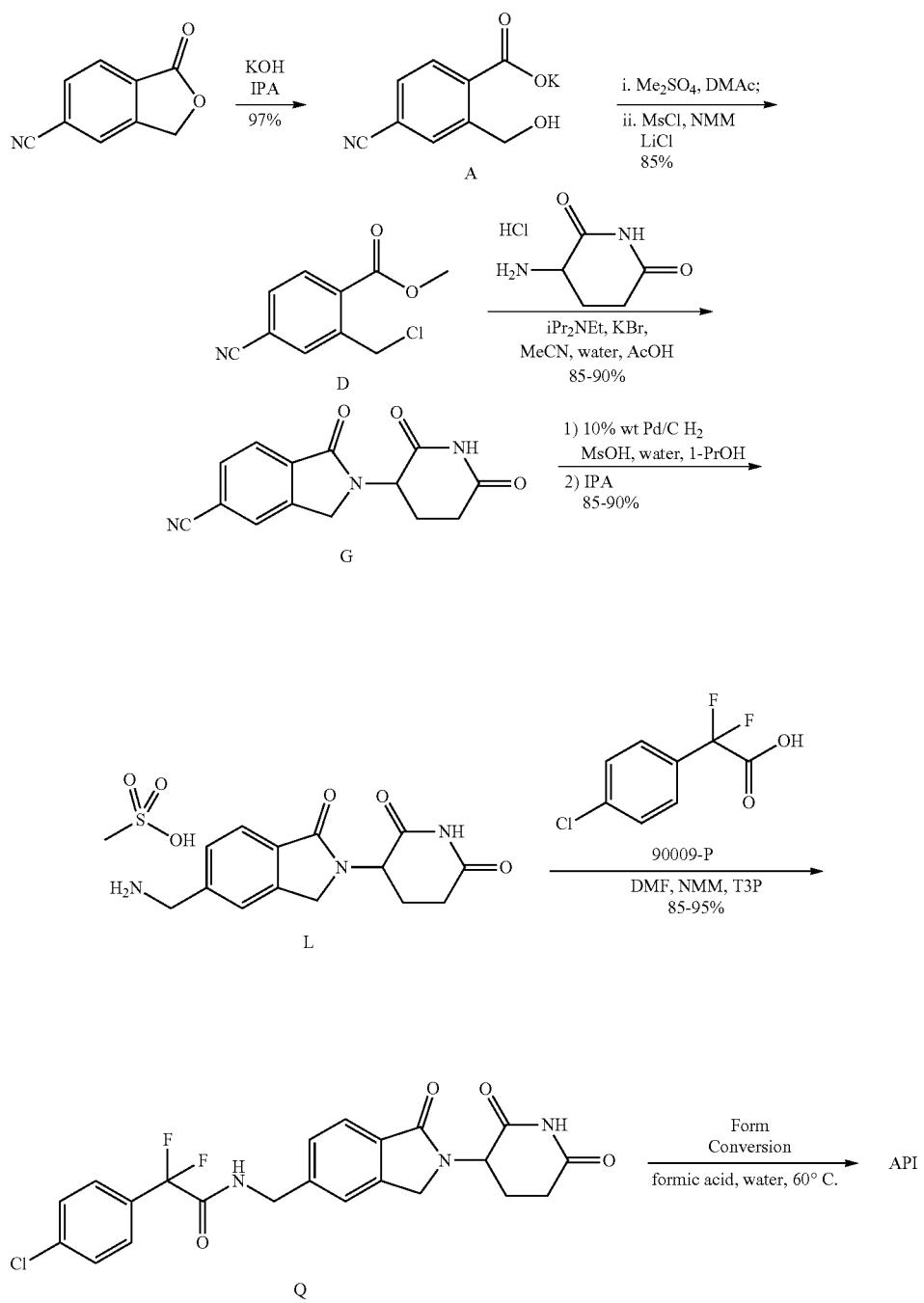

Overall yield of the title compound in this process is about 53%. The HPLC purity of polymorph Form C is obtained in this process is >99.9%. No detectable impurities were found in the final product.

The synthetic steps are described below:

Step 1: Synthesis of potassium 4-cyano-2-(hydroxymethyl)benzoate

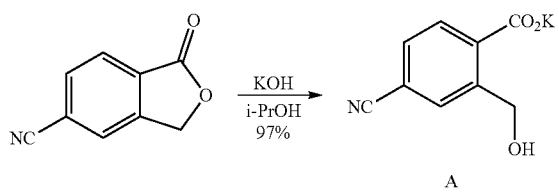

A slurry of the lactone (100.0 g) in i-PrOH (990 mL) and water (10 mL) was stirred in a reactor at ambient temperature. Potassium hydroxide (43.6 g as 86.9 wt % pellets, 1.08 equiv.) was charged as a solid. The resulting slurry was heated to $T_i$=35-40° C. and held at that temperature for 2 h. The slurry was cooled to 20-25° C., and then was filtered. The cake was washed with a mixture of i-PrOH and water. The cake was dried at 20-25° C. under vacuum and a $N_2$ sweep. Typical yield was 97%. $^1$H NMR (300 MHz, DMSO-d6) 4.50 (d, J=6 Hz, 2H), 7.34 (t, J=6 Hz, 1H), 7.62 (d, J=9 Hz, 1H), 7.66 (s, 1H), 7.78 (d, J=9 Hz, 1H).

Step 2: Synthesis of methyl 2-(chloromethyl)-4-cyanobenzoate

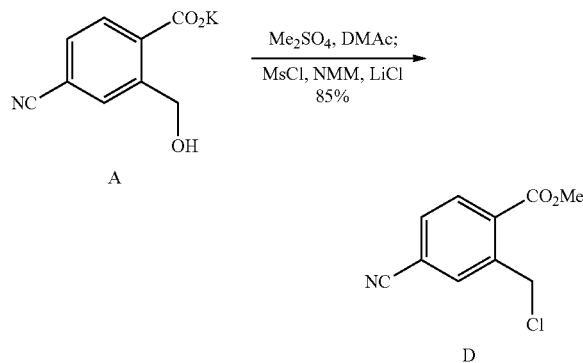

The K salt A (50.0 g) was slurried in DMAc (500 mL) at 10° C. in a three neck flask with overhead stirring. $Me_2SO_4$ (33.7 g, 25.3 mL, 1.05 equiv.) was added over 30-60 minutes at 10° C. The resulting slurry was aged at this temperature for 3 h. NMM (2.0 equiv.) was then added to the slurry, followed by the slow addition of MsCl over 30 minutes, maintaining 10-15° C. The resulting slurry was aged at this temperature for 30 minutes. LiCl (1.0 equiv.) was added as a solid in a single portion. The resulting slurry was heated to 35-40° C. for 1-2 h. The slurry was cooled to 20-25° C. over 30-60 minutes. $H_2O$ (200 mL) was added over 20 minutes to the reaction slurry, maintaining 25-30° C. The resulting solution was then seeded with the desired product. After 20-30 minutes, $H_2O$ addition (500 mL) resumed over 2 h. After 1-2 h aging, the slurry was filtered. The cake was washed with 3:2 $H_2O$:DMAc (200 mL) then with $H_2O$ (100 mL). The obtained solid was dried at 20-25° C. under vacuum and a $N_2$ sweep. Typical yield was 85%. $^1$H NMR (300 MHz, CDCl3-d) 3.97 (s, 3H), 5.04 (s, 2H), 7.69 (dd, J=3, 9 Hz, 1H), 7.90 (d, J=3 Hz, 1H), 8.06 (d, J=9 Hz, 1H).

Step 3: Synthesis of 2-(2,6-dioxopiperidin-3-yl)-1-oxoisoindoline-5-carbonitrile

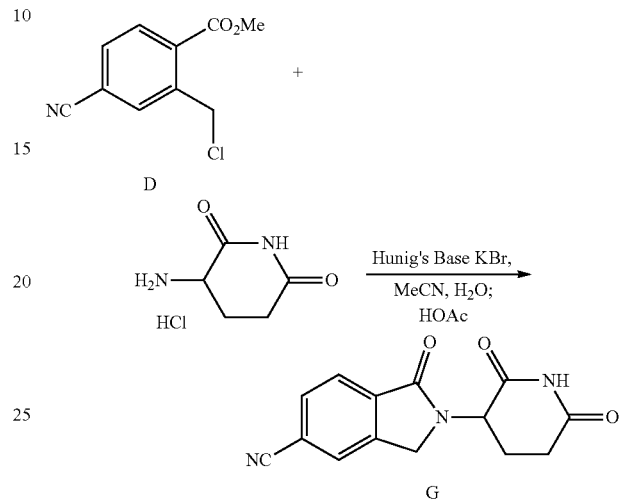

To a 100 mL reactor was charged D (7.00 g), 3-aminopiperidine-2,6-dione hydrochloride (6.05 g), and potassium bromide (3.97 g). followed by acetonitrile (56 mL), water (3.5 mL), and diisopropylethylamine (13.1 mL). The system, including reactor and pipes, was inserted by blowing gently with nitrogen, heated to 75-80° C. and aged (16 hours). The reaction was then cooled to 20° C. over 1 h. Glacial acetic acid (0.48 mL) was charged, then aged (1 h). Water (59.5 mL) was then charged to the mixture over 2 hours, and then the mixture was aged (1 h). Upon completion of the aging process, the reaction was filtered and the wet cake was then washed with a mixture of (1:1) acetonitrile:water (14 g), then washed with water (14 g). The resulting wet cake was then dried in a vac oven at 20° C. with a nitrogen bleed to yield G (7.00 g) as a light blue/purple solid. Typical yields are 75-90%. $^1$H NMR (300 MHz, DMSO-$d_6$) δ ppm 11.03 (s, 1H), 8.16 (s, 1H), 7.99 (dd, J=7.80, 0.90 Hz, 1H), 7.91 (d, J=7.80 Hz, 1H), 5.15 (dd, J=13.26, 5.10 Hz, 1H), 4.49 (q, J=18 Hz, 2H), 2.92 (ddd, J=17.5, 13.5, 5.4 Hz, 1H), 2.60 (br d, J=17.7 Hz, 1H), 2.48-2.349 (m, 1H), 2.07-1.99 (m, 1H); Anal. Calcd for $C_{14}H_{11}N_3O_3$: C, 62.45; H, 4.12; N, 15.61; O, 17.83. Found: C, 62.17; H, 4.02; N, 15.57.

Step 4: Synthesis of 3-(5-(aminomethyl)-1-oxoisoindolin-2-yl)piperidine-2,6-dione methanesulfonic acid

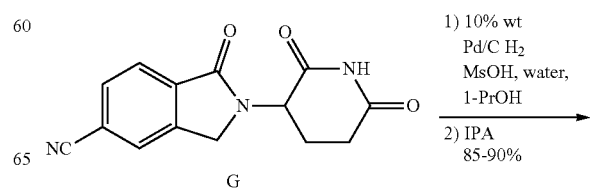

-continued

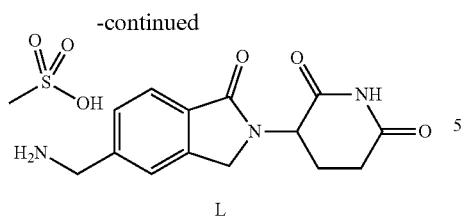

L

To a slurry of 2-(2,6-dioxopiperidin-3-yl)-1-oxoisoindoline-5-carbonitrile (G, 20 g, 74.3 mmol), 5% Pd/C (1.5 g, 7.5% wt), water (100 mL) and n-propanol (44 mL) was added methanesulfonic acid (10.8 g, 112 mmol). The mixture was agitated under 35 to 45 psi of $H_2$ pressure at 25 to 35° C. for at least 7 h and then filtered over Celite at 25 to 35° C. The solid was washed with n-propanol and water (1:4 by vol, 20 mL). The combined filtrate was extracted with anisole (120 mL) twice. To the resulting aqueous layer was added IPA (280 mL) and seeded at 30° C. followed by additional IPA (180 mL). The batch was cooled to 0 to 10° C., filtered and washed with a mixture of IPA and water (30 mL, 4:1 by volume) then IPA (40 mL). The solid was dried under vacuum at 40° C. to give 3-(5-(aminomethyl)-1-oxoisoindolin-2-yl)piperidine-2,6-dione methanesulfonic acid (L) as white solid (22.8 g, 83% yield). $^1$H NMR (300 MHz, DMSO-$d_6$) δ ppm 1.94-2.08 (m, 1H) 2.32 (s, 3H) 2.41 (br dd, J=13.07, 4.36 Hz, 1H) 2.54-2.68 (m, 1H) 2.80-3.04 (m, 1H) 4.17 (s, 2H) 4.41 (dd, J=26.60, 18.20 Hz, 2H) 5.13 (dd, J=13.25, 5.00 Hz, 1H) 7.60 (d, J=7.89 Hz, 1H) 7.69 (s, 1H) 7.79 (d, J=7.79 Hz, 1H) 8.24 (br s, 3H) 11.00 (br s, 1H). MS (ESI) m/z 274 [M+1]$^+$.

Alternate Step 4: 3-(5-(aminomethyl)-1-oxoisoindolin-2-yl)piperidine-2,6-dione Methanesulfonic acid To a slurry of 2-(2,6-dioxopiperidin-3-yl)-1-oxoisoindoline-5-carbonitrile (50 g, 186 mmol), 10% palladium on carbon, 50% water-wet (5.0 g) and 1-PrOH (500 mL) was added methanesulfonic acid (26.8 g, 279 mmol) followed by two rinses of 1-PrOH (10 mL each). 1-PrOH (480 mL) was added to the resulting slurry. The mixture was agitated under 35 to 45 psi of $H_2$ pressure at 35 to 45° C. for at least 5 hours and then cooled to 20 to 30° C. followed by addition of water (700 mL) and agitation at 20 to 30° C. for at least 1 h. To this mixture was added Si-Thiol (11.8 g, Silicycle, 40-63 um, loading: 1.30 mmol/g) and the resulting mixture was agitated at 20 to 30° C. for 18 hours. The mixture was filtered over Celite (10 g) and filtered solids were washed twice with 1-PrOH:water (1:1 by vol, 50 mL). The process were repeated 4 times before the filtrates were combined in one batch as 200 g scale reaction for downstream process.

The combined filtrates (200 g scale) were vacuum distilled to 200 to 240 mL batch volume followed by continuous vacuum distillation while charging 1-PrOH until batch water content reached 20 to 30% wt. The resulting reaction mixture was cooled to 20 to 25° C. over 1 h and held at 20 to 25° C. for at least 2 hours. The mixture was filtered, washed with 1-PrOH:water (200 mL, 4:1 by vol) and 1-PrOH (300 mL), and dried under vacuum at 40 to 50° C. to give 3-(5-(aminomethyl)-1-oxoisoindolin-2-yl)piperidine-2,6-dione methanesulfonic acid as white solid (237 g, 88% yield). $^1$H NMR (300 MHz, DMSO-$d_6$) δ ppm 1.94-2.08 (m, 1H) 2.32 (s, 3H) 2.41 (br dd, J=13.07, 4.36 Hz, 1H) 2.54-2.68 (m, 1H) 4.17 (s, 2H) 4.41 (dd, J=26.60, 18.20 Hz, 2H) 5.13 (dd, J=13.25, 5.00 Hz, 1H) 7.60 (d, J=7.89 Hz, 1H) 7.69 (s, 1H) 7.79 (d, J=7.79 Hz, 1H) 8.24 (br s, 3H) 11.00 (br s, 1H). MS (ESI) m/z 274 [M+1]$^+$.

Step 5: Synthesis of 2-(4-chlorophenyl)-N-((2-(2,6-dioxopiperidin-3-yl)-1-oxoisoindolin-5-yl)methyl)-2,2-difluoroacetamide

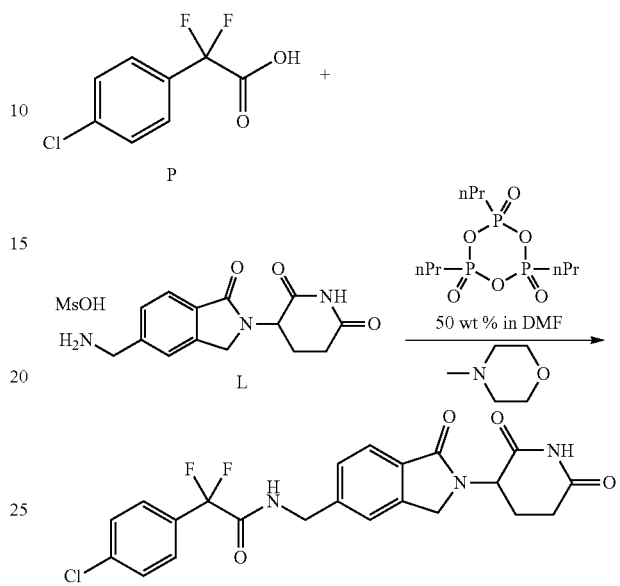

To a jacketed 3-neck round bottom flask was charged L (55 g), 2-(4-chlorophenyl)-2,2-difluoroacetic acid (33.8 g), DMF (495 mL), and N-methylmorpholine (49.6 mL). 1-Propylphosphonic anhydride (174 mL as a 50 wt % solution in DMF) was then charged to the slurry keeping the internal temperature below 40° C. Upon complete addition, heat the reaction mixture between 35-40° C. for no less than 12 hours. Additional DMF (27.5 mL) was added followed by water (144 mL) keeping the internal temperature at between 15-20° C. The mixture was seeded with 2-(4-chlorophenyl)-N-((2-(2,6-dioxopiperidin-3-yl)-1-oxoisoindolin-5-yl)methyl)-2,2-difluoroacetamide, and held for 2 h at 20° C. Additional water (401 mL) was charged over 5 h. The mixture was then filtered and the wet cake was washed with 60 wt % DMF in water (55 g), followed by water washes. The wet cake was then dried in a vacuum oven at 22° C. with a nitrogen purge to yield a white powder (65.5 g). Typical isolated yields were 85-95%. $^1$H NMR (300 MHz, DMSO-$d_6$) δ ppm 2.00 (dtd, J=12.61, 5.25, 5.25, 2.21 Hz, 1H) 2.38 (qd, J=13.22, 4.43 Hz, 1H) 2.56-2.65 (m, 1H) 2.91 (ddd, J=17.47, 13.66, 5.34 Hz, 1H) 4.24-4.49 (m, 4H) 5.10 (dd, J=13.28, 5.19 Hz, 1H) 7.37 (d, J=7.78 Hz, 1H) 7.40 (s, 1H) 7.58-7.64 (m, 4H) 7.68 (d, J=7.78 Hz, 1H) 9.68 (t, J=6.10 Hz, 1H) 10.58 (s, 1H); MS (ESI) m/z 462 [M+1]$^+$; Anal. Calcd for $C_{22}H_{18}ClF_2N_3O_4$: C, 57.21; H, 3.93; Cl, 7.68; F, 8.23; N, 9.10; O, 13.86. Found: C, 56.96; H, 3.80; N, 9.14.

Step 5A: Synthesis of methyl 2-(4-chlorophenyl)-2,2-difluoroacetate

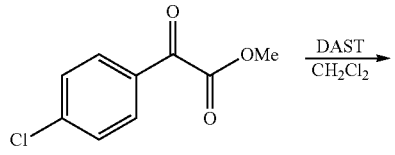

47

-continued

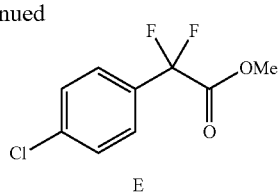

E

To a reactor was charged methyl 2-(4-chlorophenyl)-2-oxoacetate, DCM and diethylaminosulfur Trifluoride (DAST). The mixture was agitated at 22-32° C. for 6-20 hours. At the end of the reaction, the batch was cooled to 0-10° C., and water was charged. The batch was stirred for 30-60 min and layers separated. The organic layer was washed with Na$_2$CO$_3$ solution once followed by water wash twice. The organic layer was concentrated to 1-1.5× at below 45° C. under reduced pressure. MTBE (2-3×) was then charged and residual DCM level was tested (target NMT 10%). The solution was drummed to be used in the next step.

Step 5B: Synthesis of
2-(4-chlorophenyl)-2,2-difluoroacetic acid

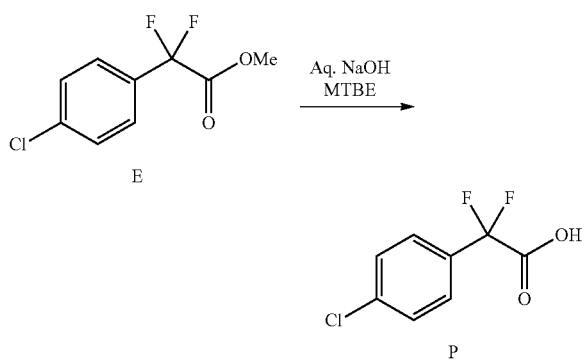

To a reactor was charged methyl 2-(4-chlorophenyl)-2,2-difluoroacetate (E) and MTBE. Aqueous NaOH (8% w/w) was added slowly to the batch to control the batch temperature at 20-30° C. The mixture was agitated at 20-30° C. for 2-4 h. At the end of the reaction, the batch was split. The aqueous layer was concentrated to 2-4× Vol under vacuum at a batch temperature of <50° C. until MeOH level was tested below or equal 0.3%. The batch was charged MTBE and cooled to 0-10° C. Concentrated HCl was added dropwise controlling the batch temperature below 25° C. until batch's pH reaches 1-2. The batch was split and organic layer was washed by water. Organic layer was concentrated under reduced vacuum under 55° C. Heptane was added and batch concentrated. Repeat adding Heptane and distill until MTBE level in batch was less than 0.5%. More heptane was added and the batch was agitated at 55-65° C. for 0.5-2 h when all solid dissolve. The batch was cooled to 10-20° C. over at least 2 h and kept at this temperature for 1-3 h. The batch was filtered and dried in oven to yield compound P. Typical yield was 75-85%. $^1$H NMR (400 MHz, CDCl$_3$) δ ppm 7.48 (d, J=8.4 Hz, 2H) 9.05 (broad, 1H); MS (ESI positive mode) m/z 205 [M−1]$^+$.

48

Step 6: Synthesis of Form C of 2-(4-chlorophenyl)-N-((2-(2,6-dioxopiperidin-3-yl)-1-oxoisoindolin-5-yl)methyl)-2,2-difluoroacetamide

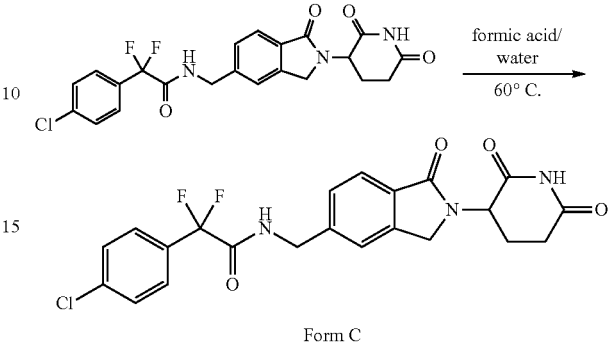

Form C

To a solution of 2-(2,6-dioxopiperidin-3-yl)-1-oxoisoindoline-5-carbonitrile (25 g, 54.1 mmol) in formic acid (262 mL) was added water (50 mL) and seed (0.5 g). The batch was agitated for 15 min and added water (212 mL) over 1 h. The batch was heated to 55 to 65° C. and agitated at 55 to 65° C. for at least 16 h followed by cooling to 15 to 25° C. The mixture was filtered and washed with a mixture of formic acid and water (1:1 by vol, 50 mL) then twice with water (50 mL). The solid was dried under vacuum at 40° C. to give 2-(4-chlorophenyl)-N-((2-(2,6-dioxopiperidin-3-yl)-1-oxoisoindolin-5-yl)methyl)-2,2-difluoroacetamide as white solid (23 g, 93% yield). $^1$H NMR (300 MHz, DMSO-d$_6$) δ ppm 1.98-2.04 (m, 1H) 2.33-2.46 (m, 1H) 2.58-2.64 (m, 1H), 2.86-2.98 (m, 1H), 4.29 (d, J=18.0 Hz, 1H), 4.43 (d, J=18 Hz, 1H), 4.46 (d, J=5.4 Hz, 2H), 5.12 (dd, J=4.8, 13.0 Hz, 1H), 7.37 (d, J=7.8 Hz, 1H), 7.40 (s, 1H) 7.58-7.64 (s, 4H), 7.68 (d, J=7.8 Hz, 1H), 9.70 (t, J=6.0 Hz, 1H) 11.01 (s, 1H); MS (ESI) m/z 462 [M+1]$^+$.

Example 4

Synthesis of Form C of 2-(4-chlorophenyl)-N-((2-(2,6-dioxopiperidin-3-yl)-1-oxoisoindolin-5-yl)methyl)-2,2-difluoroacetamide

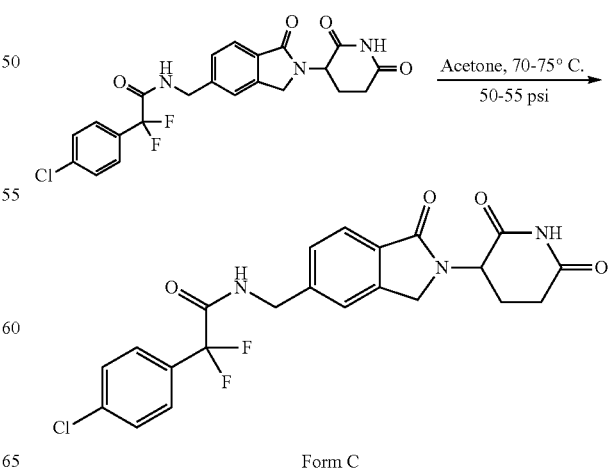

Form C

Compound Q (6.5 g) was added to acetone (195 ml) in a reactor. The reactor was pressurized with nitrogen to 30-35 psig. The reaction mixture was heated to 70-75° C. with agitation. The pressure was then adjusted with nitrogen to 50-55 psig. The mixture was agitated at 70-75° C. for minimum 24 hours, then cooled to room temperature (20-25° C.). The pressure was released and the mixture was filtered. The cake was washed with acetone. The resulting solid was dried in oven to obtain Form C of 2-(4-chlorophenyl)-N-((2-(2,6-dioxopiperidin-3-yl)-1-oxoisoindolin-5-yl)methyl)-2,2-difluoroacetamide as white to off-white solid (5.9 g, 90% yield). XRPD confirmed the product as Form C of 2-(4-chlorophenyl)-N-((2-(2,6-dioxopiperidin-3-yl)-1-oxoisoindolin-5-yl)methyl)-2,2-difluoroacetamide.

Example 5

Synthesis of methyl 4-cyano-2-(((methylsulfonyl)oxy)methyl)benzoate

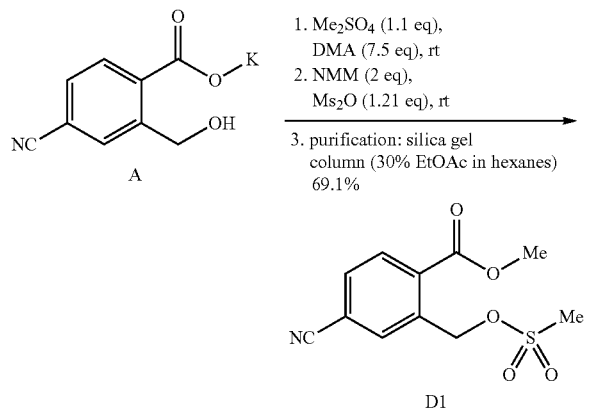

Compound A (6.89 g, 32.0 mmol, 1 eq) was slurred in DMA (50 mL) at 20-25° C. in a water bath and $Me_2SO_4$ (4.44 g, 35.2 mmol, 1.1 eq) was added dropwise over 20 min. The resulting slurry was aged at this temperature for 3 h. NMM (7.04 mL, 64.0 mmol, 2 eq) was added to the slurry, followed by a slow addition of a solution of $Ms_2O$ (6.74 g, 38.72 mmol, 1.21 eq) in DMA (15 mL) over 20 min at 20-25° C. in a water bath. The reaction mixture was stirred at room temperature overnight. Water was added to the mixture while keeping temperature <20° C. until a homogenous solution was obtained. More water was added until a slurry formed, which was filtered. The solid was washed with water, dissolved in DCM and dried over $Na_2SO_4$. Filtration and concentration gave a crude product, which was purified by CombiFlash (dry loading, eluent: 30% EtOAc in hexanes) to give Compound D (5.95 g, 69.1%) as a white solid.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed:

1. A process for preparing 2-(4-chlorophenyl)-N-((2-(2,6-dioxopiperidin-3-yl)-1-oxoisoindolin-5-yl)methyl)-2,2-difluoroacetamide comprising contacting Compound M with 2-(4-chlorophenyl)-2,2-difluoroacetic acid in the presence of a base and 1-propylphosphonic anhydride in a solvent, under conditions suitable to provide 2-(4-chlorophenyl)-N-((2-(2,6-dioxopiperidin-3-yl)-1-oxoisoindolin-5-yl)methyl)-2,2-difluoroacetamide, wherein Compound M is selected from methanesulfonate, hydrochloride, sulfate, phosphate and acetate salt of 3-(5-(aminomethyl)-1-oxoisoindolin-2-yl)piperidine-2,6-dione.

2. The process of claim 1, wherein the process comprises contacting Compound L with 2-(4-chlorophenyl)-2,2-difluoroacetic acid in the presence of a base and 1-propylphosphonic anhydride in a solvent, under conditions suitable to provide 2-(4-chlorophenyl)-N-((2-(2,6-dioxopiperidin-3-yl)-1-oxoisoindolin-5-yl)methyl)-2,2-difluoroacetamide.

3. The process of claim 1, wherein the base is N-methyl morpholine.

4. The process of claim 1, wherein the solvent is dimethylformamide.

5. The process of claim 1 further comprising contacting Compound G with a reducing agent in a solvent followed by contacting with an acid selected from methanesulfonic acid, hydrochloric acid, sulfuric acid, phosphoric acid, or acetic acid, under conditions suitable to provide Compound M.

6. The process of claim 5, wherein the reducing agent is 5% or 10% palladium on carbon.

7. The process of claim 5, wherein the solvent comprises one or more of N-methyl pyrrolidone, 1 propanol, isopropyl alcohol, ethanol and tetrahydrofuran.

8. The process of claim 1 further comprising contacting Compound G with a reducing agent in a solvent followed by contacting with an methanesulfonic acid, under conditions suitable to provide Compound L.

9. The process of claim 8, wherein the reducing agent comprises 10% palladium on carbon.

10. The process of claim 8, wherein the solvent comprises water and 1-propanol.

11. The process of claim 8, wherein the solvent comprises water and isopropanol.

12. The process of claim 8 further comprising contacting Compound X

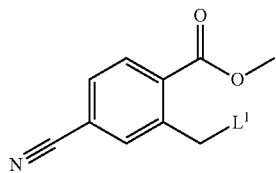

wherein $L^1$ is a leaving group;
with 3-aminopiperidine-2,6-dione hydrochloride in the presence of a salt, followed by a solvent and a base, under conditions suitable to provide Compound G.

13. The process of claim 12, wherein $L^1$ is halogen or methanesulfonate.

14. The process of claim 8 further comprising contacting Compound D

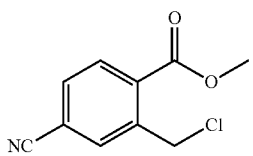

with 3-aminopiperidine-2,6-dione hydrochloride in the presence of a salt, followed by a solvent and a base, under conditions suitable to provide Compound G.

15. The process of claim 12, wherein the salt is potassium bromide or potassium iodide.

16. The process of claim 12, wherein the base is N,N-diisopropylethylamine.

17. The process of claim 12, wherein the solvent comprises acetonitrile.

18. The process of claim 12, wherein the solvent comprises acetonitrile and water.

19. The process of claim 12 further comprising contacting Compound A

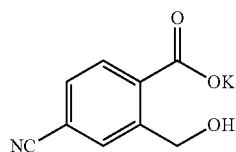

with 1) dimethyl sulfate in a solvent; 2) a base; 2) methanesulfonyl chloride; and 4) lithium chloride, under conditions suitable to provide Compound D.

20. The process of claim 14, wherein the base is N-methyl morpholine.

21. The process of claim 14, wherein the solvent is dimethylacetamide.

22. The process of claim 19 further comprising contacting 1-oxo-1,3-dihydroisobenzofuran-5-carbonitrile

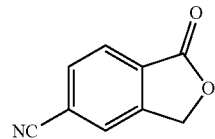

with a base in a solvent under conditions suitable to provide Compound A.

23. The process of claim 22, wherein the base is potassium hydroxide.

24. The process of claim 22, wherein the solvent is isopropyl alcohol.

* * * * *